US006410324B1

(12) United States Patent
Bennett et al.

(10) Patent No.: US 6,410,324 B1
(45) Date of Patent: Jun. 25, 2002

(54) ANTISENSE MODULATION OF TUMOR NECROSIS FACTOR RECEPTOR 2 EXPRESSION

(75) Inventors: C. Frank Bennett, Carlsbad; Andrew T. Watt, Vista, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/844,634

(22) Filed: Apr. 27, 2001

(51) Int. Cl.$^7$ .......................... C12Q 1/68; C07H 21/04; C12N 15/85
(52) U.S. Cl. .......................... 435/375; 435/6; 435/91.1; 435/325; 435/366; 536/23.1; 536/24.31; 536/24.33; 536/24.5
(58) Field of Search .......................... 435/6, 325, 366, 435/375; 536/23.1, 24.5, 25.3; 514/44

(56) References Cited

U.S. PATENT DOCUMENTS 5,801,154 A * 9/1998 Baracchini et al. ............ 514/44
5,951,455 A * 9/1999 Cowsert ...................... 495/375

OTHER PUBLICATIONS

Andrea D. Branch, A good antisense molecule is hard to find, TIBS 23—Feb. 1998, pp. 45–50.*
W. Michael Flanagan et al., Cellular penetration and antisense activity by a phenoxazine–substituted heptanucleotide, Nature Biotech 17, Jan. 1999, pp. 48–52.*
Agostini et al., Expression of tumor necrosis factor–receptor superfamily members by lung T lymphocytes in interstitial lung disease, Am. J. Respir. Crit. Care Med., 1996, 153:1359–1367.
Beltinger et al., Physical mapping and genomic structure of the human TNFR2 gene, Genomics, 1996, 35:94–100.
Bruce et al., Altered neuronal and microglial responses to excitotoxic and ischemic brain injury in mice lacking TNF receptors, Nat. Med., 1996, 2:788–794.
Fernandez–Real et al., Polymorphism of the tumor necrosis factor–alpha receptor 2 gene is associated with obesity, leptin levels, and insulin resistance in young subjects and diet–treated type 2 diabetic patients, Diabetes Care, 2000, 23:831–837.

Geurts et al., Identification of TNFRSF1B as a novel modifier gene in familial combined hyperlipidemia, Hum. Mol. Genet., 2000, 9:2067–2074.
Glenn et al., Linkage and association of tumor necrosis factor receptor 2 locus with hypertension, hypercholesterolemia and plasma shed receptor, Hum. Mol. Genet., 2000, 9:1943–1949.
Hohjoh et al., Significant association of the tumor necrosis factor receptor 2 (TNFR2) gene with human narcolepsy, Tissue Antigens, 2000, 56:446–448.
Komata et al., Association of tumor necrosis factor receptor 2 (TNFR2) polymorphism with susceptibility to systemic lupus erythematosus, Tissue Antigens, 1999, 53:527–533.
Lucas et al., Crucial role of tumor necrosis factor (TNF) receptor 2 and membrane–bound TNF in experimental cerebral malaria, Eur. J. Immunol., 1997, 27:1719–1725.
Schall et al., Molecular cloning and expression of a receptor for human tumor necrosis factor, Cell, 1990, 61:361–370.
Shen et al., Inhibition of p75 Tumor Necrosis Factor Receptor by Antisense Oligonucleotides Increases Hypoxic Injury and b–Amyloid Toxicity in Human Neuronal Cell Line, J. Biol. Chem., 1997, 272:3550–3553.
Suvannavehj et al., Divergent roles for p55 and p75 tumor necrosis factor receptors in the pathogenesis of MOG(35–55)—induced experimental autoimmune encephalomyelitis, Cell Immunol., 2000, 205:24–33.
Tracey et al., Tumor necrosis factor: a pleiotropic cytokine and therapeutic target, Ann. Rev. Med., 1994, 45:491–503.
van Greevenbroek et al., Soluble receptors for tumor necrosis factor–alpha (TNF–R p55 and TNF–R p75) in familial combined hyperlipidemia, Atherosclerosis, 2000, 153:1–8.

* cited by examiner

Primary Examiner—John L. LeGuyader
Assistant Examiner—M Schmidt
(74) Attorney, Agent, or Firm—Licata & Tyrell P.C.

(57) ABSTRACT

Antisense compounds, compositions and methods are provided for modulating the expression of Tumor Necrosis Factor Receptor 2. The compositions comprise antisense compounds, particularly antisense oligonucleotides, targeted to nucleic acids encoding Tumor Necrosis Factor Receptor 2. Methods of using these compounds for modulation of Tumor Necrosis Factor Receptor 2 expression and for treatment of diseases associated with expression of Tumor Necrosis Factor Receptor 2 are provided.

26 Claims, No Drawings

ANTISENSE MODULATION OF TUMOR NECROSIS FACTOR RECEPTOR 2 EXPRESSION

FIELD OF THE INVENTION

The present invention provides compositions and methods for modulating the expression of Tumor Necrosis Factor Receptor 2. In particular, this invention relates to compounds, particularly oligonucleotides, specifically hybridizable with nucleic acids encoding Tumor Necrosis Factor Receptor 2. Such compounds have been shown to modulate the expression of Tumor Necrosis Factor Receptor 2.

BACKGROUND OF THE INVENTION

One of the principal mechanisms by which cellular regulation is effected is through the transduction of extracellular signals into intracellular signals that in turn modulate biochemical pathways. Examples of such extracellular signaling molecules include growth factors, cytokines, and chemokines. The cell surface receptors of these molecules and their associated signal transduction pathways are therefore one of the principal means by which cellular behavior is regulated. Because cellular phenotypes are largely influenced by the activity of these pathways, it is currently believed that a number of disease states and/or disorders are a result of either aberrant activation or functional mutations in the molecular components of signal transduction pathways.

For example, the polypeptide cytokine tumor necrosis factor (TNF) is normally produced during infection, injury, or invasion where it serves as a pivotal mediator of the inflammatory response. In recent years, a number of in vivo animal and human studies have demonstrated that overexpression TNF by the host in response to disease and infection is itself responsible for the pathological consequences associated with the underlying disease. For example, septic shock as a result of massive bacterial infection has been attributed to infection-induced expression of TNF. Thus, systemic exposure to TNF at levels comparable to those following massive bacterial infection has been shown to result in a spectrum of symptoms (shock, tissue injury, capillary leakage, hypoxia, pulmonary edema, multiple organ failure, and high mortality rate) that is virtually indistinguishable from septic shock syndrome (Tracey and Cerami, *Annu. Rev. Med.*, 1994, 45, 491–503). Further evidence has been provided in animal models of septic shock, in which it has been demonstrated that systemic exposure to anti-TNF neutralizing antibodies block bacterial-induced sepsis (Tracey and Cerami, *Annu. Rev. Med.*, 1994, 45, 491–503). In addition to these acute effects, chronic exposure to low-dose TNF, results in a syndrome of cachexia marked by anorexia, weight loss, dehydration, and depletion of whole-body protein and lipid. Chronic production of TNF has been implicated in a number of diseases including AIDS and cancer (Tracey and Cerami, *Annu. Rev. Med.*, 1994, 45, 491–503). To date, two distinct TNF cells surface receptors, known as Tumor necrosis factor receptor 1 and Tumor necrosis factor receptor 2, have been described. Molecular analysis of Tumor necrosis factor receptor 1 and Tumor necrosis factor receptor 2 have shown that the two receptors share little homology in their intracellular domains and appear to activate distinct intracellular pathways (Tracey and Cerami, *Annu. Rev. Med.*, 1994, 45, 491–503).

Tumor necrosis factor (TNFR2, also known as CD120b, p75 TNFR and TNFR-beta receptor) was first cloned in 1990 (Schall et al., *Cell*, 1990, 61, 361–370.) and mapped to chromosomal locus 1p36.2 in 1996 (Beltinger et al., *Genomics*, 1996, 35, 94–100).

Bruce et al. used targeted gene expression to generate mice lacking both TNFRs and concluded that drugs which target the TNF signaling pathways may prove beneficial in treating stroke or traumatic brain injury (Bruce et al., *Nat. Med.*, 1996, 2, 788–794.). Tumor necrosis factor receptor 2 knockout mice were also used to establish a crucial role for Tumor necrosis factor receptor 2 in experimental cerebral malaria (Lucas et al., *Eur. J. Immunol.*, 1997, 27, 1719–1725) and autoimmune encephalomyelitis (Suvannavejh et al., *Cell Immunol.*, 2000, 205, 24–33), models for human cerebral malaria and multiple sclerosis, respectively.

Agostini et al. have determined that Tumor necrosis factor receptor 2 is present at high density on T cells and may play a role in the immune regulatory mechanisms that lead to alveolitis in the pulmonary microenvironment of interstitial lung disease (Agostini et al., *Am. J. Respir. Crit. Care Med.*, 1996, 153, 1359–1367). Tumor necrosis factor receptor 2 is implicated in human metabolic disorders of lipid metabolism and associated with obesity and insulin resistance (Fernandez-Real et al., *Diabetes Care*, 2000, 23, 831–837), familial combined hyperlipidemia (Geurts et al., *Hum. Mol. Genet.*, 2000, 9, 2067–2074.; van Greevenbroek et al., *Atherosclerosis*, 2000, 153, 1–8), hypertension and hypercholesterolemia (Glenn et al., *Hum. Mol. Genet.*, 2000, 9, 1943–1949). Tumor necrosis factor receptor 2 has also recently been associated with human narcolepsy (Komata et al., *Tissue Antigens*, 1999, 53, 527–533). In addition, Tumor necrosis factor receptor 2 polymorphism appears to lead to susceptibility to systemic lupus erythematosus (Hohjoh et al., *Tissue Antigens*, 2000, 56, 446–448).

An antisense oligonucelotide targeting the initiation site of the human Tumor necrosis factor receptor 2 gene was used to inhibit Tumor necrosis factor receptor 2 expression in a human neuronal cell line (Shen et al., *J. Biol. Chem.*, 1997, 272, 3550–3553).

Currently, there are no known therapeutic agents which effectively inhibit the synthesis of Tumor necrosis factor receptor 2 and investigative strategies aimed at modulating Tumor necrosis factor receptor 2 function have involved the use of inhibitors such as antibodies and antisense oligonucleotides.

Antisense technology is emerging as an effective means of reducing the expression of specific gene products and may therefore prove to be uniquely useful in a number of therapeutic, diagnostic and research applications involving modulation of Tumor necrosis factor receptor 2 expression.

The present invention provides compositions and methods for modulating the expression of Tumor necrosis factor receptor 2.

SUMMARY OF THE INVENTION

The present invention is directed to compounds, particularly antisense oligonucleotides, which are targeted to a nucleic acid encoding Tumor Necrosis Factor Receptor 2, and which modulate the expression of Tumor Necrosis Factor Receptor 2. Pharmaceutical and other compositions comprising the compounds of the invention are also provided. Further provided are methods of modulating the expression of Tumor Necrosis Factor Receptor 2 in cells or tissues comprising contacting said cells or tissues with one or more of the antisense compounds or compositions of the invention. Further provided are methods of treating an animal, particularly a human, suspected of having or being prone to a disease or condition associated with expression of Tumor Necrosis Factor Receptor 2 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding Tumor Necrosis Factor Receptor 2, ultimately modulating the amount of Tumor Necrosis Factor Receptor 2 produced. This is accomplished by providing antisense compounds which specifically hybridize with one or more nucleic acids encoding Tumor Necrosis Factor Receptor 2. As used herein, the terms "target nucleic acid" and "nucleic acid encoding Tumor Necrosis Factor Receptor 2" encompass DNA encoding Tumor Necrosis Factor Receptor 2, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of Tumor Necrosis Factor Receptor 2. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding Tumor Necrosis Factor Receptor 2. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Tumor Necrosis Factor Receptor 2, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thiofor- macetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$ $CH_3$, O($CH_2$)$_n$O$CH_3$, O($CH_2$)$_n$N$H_2$, O($CH_2$)$_n$$CH_3$, O($CH_2$)$_n$ON$H_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i. e., 2'-O—CH$_2$—O—CH$_2$—N(CH$_2$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH$_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2-H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering,* pages 858–859, Kroschwitz, J. I., ed. John Wiley & Sons, 1990, those disclosed by Englisch et al., *Angewandte Chemie,* International Edition, 1991, 30, 613, and those disclosed by Sanghvi, Y. S., Chapter 15, *Antisense Research and Applications,* pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications,* CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416, 016; 5,417,978; 5,462,854; 5,469,854; 5,512,295; 5,527, 528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of Tumor Necrosis Factor Receptor 2 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding Tumor Necrosis Factor Receptor 2, enabling sandwich and other assays to easily be constructed to exploit this fact. Hybridization of the antisense oligonucleotides of the invention with a nucleic acid encoding Tumor Necrosis Factor Receptor 2 can be detected by means known in the art. Such means may include conjugation of an enzyme to the oligonucleotide, radiolabelling of the oligonucleotide or any other suitable detection means. Kits using such detection means for detecting the level of Tumor Necrosis Factor Receptor 2 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate,. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly (methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. applications Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms,* Lieberman, Rieger and Banker (Eds.), 1988, Marcel Dekker, Inc., New York, N.Y.:, volume 1, p. 199; Rosoff, in *Pharmaceutical Dosage Forms,* Lieberman, Rieger and Banker (Eds.), 1988, Marcel Dekker, Inc., New York, N.Y., Volume 1, p. 245;

Block in *Pharmaceutical Dosage Forms,* Lieberman, Rieger and Banker (Eds.), 1988, Marcel Dekker, Inc., New York, N.Y., volume 2, p. 335; Higuchi et al., in *Remington's Pharmaceutical Sciences,* Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms,* Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms,* Lieberman, Rieger and Banker (Eds.), 1988, Marcel Dekker, Inc., New York, N.Y., volume 1, p. 285; Idson, in *Pharmaceutical Dosage Forms,* Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms,* Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms,* Lieberman, Rieger and Banker (Eds.), 1988, Marcel Dekker, Inc., New York, N.Y., volume 1, p. 335; Idson, in *Pharmaceutical Dosage Forms,* Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms,* Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms,* Lieberman, Rieger and Banker (Eds.), 1988, Marcel Dekker, Inc., New York, N.Y., volume 1, p. 245; Idson, in *Pharmaceutical Dosage Forms,* Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.) . U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms,* Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms,* Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems,* 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems,* 1991, p.92); and perfluorochemical emulsions, such as FC-43. Takahashi et al., *J. Pharm. Pharmacol.,* 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems,* 1991, p.92; Muranishi, *Critical Reviews in Therapeutic Drug Carrier Systems,* 1990, 7, 1–33; El Hariri et al., *J. Pharm. Pharmacol.,* 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics,* 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me—C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.)

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxytetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites

2'-(Dimethylaminooxyethoxy) Nucleoside Amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirrred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl Uridine To 0.5 g (1.3 mmol) of 2'-O-[2(2-N,N-dimethylaminoethoxy)ethyl]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2
Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or U.S. Pat. No. 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3
Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]--[2'-deoxy]--[2'-O-Me] Chimeric Phosphorothioate Oligonucleotides Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]--[2'-deoxy]--[2'-O-(Methoxyethyl)] Chimeric Phosphorothioate Oligonucleotides

[2'-O-(2-methoxyethyl)]--[2'-deoxy]--[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]--[2'-deoxy Phosphorothioate]--[2'-O-(2-Methoxyethyl) Phosphodiester] Chimeric Oligonucleotides

[2'-O-(2-methoxyethyl phosphodiester]--[2'-deoxy phosphorothioate]--[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8
Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9
Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 6 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

HuVEC Cells

The human umbilical vein endothilial cell line HuVEC was obtained from the American Type Culure Collection (Manassas, Va.). HuVEC cells were routinely cultured in EBM (Clonetics Corporation Walkersville, Md.) supplemented with SingleQuots supplements (Clonetics Corporation, Walkersville, Md.). Cells were routinely passaged by trypsinization and dilution when they reached 90% confluence were maintained for up to 15 passages. Cells were seeded into 96-well plates (Falcon-Primaria #3872) at a density of 10000 cells/well for use in RT-PCR analysis.

For Northern blotting or other analyses, cells may be seeded onto 100 mm or other standard tissue culture plates and treated similarly, using appropriate volumes of medium and oligonucleotide.

3T3-L1 Cells

The mouse embryonic adipocyte-like cell line 3T3-L1 was obtained from the American Type Culure Collection (Manassas, Va.). 3T3-L1 cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 80% confluence. Cells were seeded into 96-well plates (Falcon-Primaria #3872) at a density of 4000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds

When cells reached 80% confluency, they were treated with oligonucleotide. For cells grown in 96-well plates, wells were washed once with 200 µL OPTI-MEM™-1 reduced-serum medium (Gibco BRL) and then treated with 130 µL of OPTI-MEM™-1 containing 3.75 µg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold)

with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10
Analysis of Oligonucleotide Inhibition of Tumor Necrosis Factor Receptor 2 Expression Antisense modulation of Tumor Necrosis Factor Receptor 2 expression can be assayed in a variety of ways known in the art. For example, Tumor Necrosis Factor Receptor 2 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology,* Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology,* Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of Tumor Necrosis Factor Receptor 2 can be quantitated in a variety of ways well known in the art, such as immunoprecipitation, Western blot analysis (immunoblotting), ELISA or fluorescence-activated cell sorting (FACS). Antibodies directed to Tumor Necrosis Factor Receptor 2 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology,* Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology,* Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology,* Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology,* Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology,* Volume 2, pp. 11.2.1–11.2.22, John Wiley & Sons, Inc., 1991.

Example 11
Poly(A)+ mRNA Isolation

Poly(A)+ mRNA was isolated according to Miura et al., *Clin. Chem.,* 1996, 42, 1758–1764. Other methods for poly(A)+ mRNA isolation are taught in, for example, Ausubel, F. M. et al., *Current Protocols in Molecular Biology,* Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12
Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13
Real-time Quantitative PCR Analysis of Tumor Necrosis Factor Receptor 2 mRNA Levels Quantitation of Tumor Necrosis Factor Receptor 2 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1×TAQMAN™ buffer A, 5.5 mM $MgCl_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 µL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 µL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human Tumor Necrosis Factor Receptor 2 were designed to hybridize to a human Tumor Necrosis Factor Receptor 2 sequence, using published sequence information (GenBank accession number NM_001066, incorporated herein as SEQ ID NO:3). For human Tumor Necrosis Factor Receptor 2 the PCR primers were:

forward primer: CACTCCCCACCTTCAATTCCT (SEQ ID NO: 4)
reverse primer: GCAGACACAAGACTGGCACTTG (SEQ ID NO: 5) and the PCR probe was: FAM-CCCAAACGGGCTGCCCTGC-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:
forward primer: GAAGGTGAAGGTCGGAGTC (SEQ ID NO: 7)
reverse primer: GAAGATGGTGATGGGATTTC (SEQ ID NO: 8) and the PCR probe was: 5' JOE-CAAGCTTCCCGTTCTCAGCC- TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse Tumor Necrosis Factor Receptor 2 were designed to hybridize to a mouse Tumor Necrosis Factor Receptor 2 sequence, using published sequence information (GenBank accession number M59378, incorporated herein as SEQ ID NO:10). For mouse Tumor Necrosis Factor Receptor 2 the PCR primers were:
forward primer: GTTTGCAGCCTCTGCCTTTG (SEQ ID NO:11)
reverse primer: AAGGCGTGGCCTTGGAA (SEQ ID NO: 12) and the PCR probe was: FAM-AGCTCCTCCTCCTGACCTTCTAATGAGCC-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were:
forward primer: GGCAAATTCAACGGCACAGT (SEQ ID NO: 14)
reverse primer: GGGTCTCGCTCCTGGAAGAT (SEQ ID NO: 15) and the PCR probe was: 5' JOE-AAGGCCGAGAATGGGAAGCTTGTCATC- TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14
Northern Blot Analysis of Tumor Necrosis Factor Receptor 2 mRNA Levels Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human Tumor Necrosis Factor Receptor 2, a human Tumor Necrosis Factor Receptor 2 specific probe was prepared by PCR using the forward primer CACTC-CCCACCTTCAATTCCT (SEQ ID NO: 4) and the reverse primer GCAGACACAAGACTGGCACTTG (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse Tumor Necrosis Factor Receptor 2, a mouse Tumor Necrosis Factor Receptor 2 specific probe was prepared by PCR using the forward primer GTTTGCAGC-CTCTGCCTTTG (SEQ ID NO:11) and the reverse primer AAGGCGTGGCCTTGGAA (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15
Antisense Inhibition of Human Tumor Necrosis Factor Receptor 2 Expression by Chimeric Phosphorothioate Oligonucleotides Having 2'-MOE Wings and a Deoxy Gap In accordance with the present invention, a series of oligonucleotides were designed to target different regions of the human Tumor Necrosis Factor Receptor 2 RNA, using published sequences (GenBank accession number NM_001066, incorporated herein as SEQ ID NO: 3, the complement of genomic sequence from GenBank accession number AL031276 containing a portion of intron 8, exon 9, intron 9 and exon 10 of human Tumor necrosis factor receptor 2, incorporated herein as SEQ ID NO: 17, GenBank accession number U52158, incorporated herein as SEQ ID NO: 18, and an mRNA variant of human Tumor necrosis factor receptor 2 contained in GenBank accession number AI379026, the complement of which is incorporated herein as SEQ ID NO: 19). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human Tumor Necrosis Factor Receptor 2 mRNA levels by quantitative real-time PCR as described in other examples herein. Data are averages from two experiments. If present, "N.D." indicates "no data".

TABLE 1

Inhibition of human Tumor Necrosis Factor Receptor 2 mRNA levels by chimeric phosphorothioate oligonucleotides having 2'-MOE wings and a deoxy gap

| ISIS # | REGION | TARGET SEQ ID NO | TARGET SITE | SEQUENCE | %INHIB | SEQ ID NO |
|---|---|---|---|---|---|---|
| 135862 | 5'UTR | 3 | 4 | tctccaggctccgctgcgct | 89 | 20 |
| 135863 | Intron: Exon Junction | 18 | 106 | ttgcatgttggcctgaggaa | 85 | 21 |
| 135864 | Coding | 3 | 198 | ctgagccggcatgtgctccc | 0 | 22 |
| 135865 | Coding | 3 | 202 | ttctctgagccggcatgtgc | 55 | 23 |
| 135866 | Coding | 3 | 218 | ctgtctggtcatagtattct | 100 | 24 |
| 135867 | Exon | 19 | 227 | tttaagagacaatttcatgc | 74 | 25 |
| 135868 | Coding | 3 | 228 | cacatctgagctgtctggtc | 89 | 26 |
| 135869 | Coding | 3 | 232 | gcagcacatctgagctgtct | 100 | 27 |
| 135870 | Coding | 3 | 258 | gcatgttggcccggcgagca | 56 | 28 |
| 135871 | Coding | 3 | 268 | gaagacttttgcatgttggc | 83 | 29 |
| 135872 | Coding | 3 | 357 | cagctcaagcactcgggaac | 67 | 30 |
| 135873 | Coding | 3 | 387 | tccacctggtcagagctaca | 77 | 31 |
| 135874 | Coding | 3 | 427 | ggtgcagatgcggttctgtt | 88 | 32 |
| 135875 | Coding | 3 | 537 | gtttcagttcctggtctggc | 24 | 33 |
| 135876 | Coding | 3 | 540 | gatgtttcagttcctggtct | 57 | 34 |
| 135877 | Coding | 3 | 554 | tgcacaccacgtctgatgtt | 0 | 35 |
| 135878 | Coding | 3 | 631 | cacgttacagatctggtggg | 52 | 36 |
| 135879 | Coding | 3 | 721 | gggtaagtgtactgcccctg | 9 | 37 |
| 135880 | Coding | 3 | 747 | tgttgggatcgtgtggacac | 16 | 38 |

TABLE 1-continued

Inhibition of human Tumor Necrosis Factor Receptor 2 mRNA levels by chimeric phosphorothioate oligonucleotides having 2'-MOE wings and a deoxy gap

| ISIS # | REGION | TARGET SEQ ID NO | TARGET SITE | SEQUENCE | %INHIB | SEQ ID NO |
|---|---|---|---|---|---|---|
| 135881 | Coding | 3 | 755 | gctgcgtgtgttgggatcgt | 79 | 39 |
| 135882 | Coding | 3 | 868 | cacaatcagtccaactggaa | 82 | 40 |
| 135883 | Coding | 3 | 946 | caagggcttcttttcacct | 67 | 41 |
| 135884 | Coding | 3 | 980 | gcaagtgaggcaccttggct | 39 | 42 |
| 135885 | Coding | 3 | 998 | cccgggccttatcggcaggc | 48 | 43 |
| 135886 | Intron | 17 | 1054 | gtcccatctacttgggaggc | 23 | 44 |
| 135887 | Coding | 3 | 1066 | ctccagggagctgctgctgg | 73 | 45 |
| 135888 | Coding | 3 | 1071 | gagctctccagggagctgct | 68 | 46 |
| 135889 | Coding | 3 | 1076 | tggccgagctctccagggag | 27 | 47 |
| 135890 | Coding | 3 | 1230 | acgttcacgatgcaggtgac | 80 | 48 |
| 135891 | Coding | 3 | 1246 | gtcagagctgctacagacgt | 77 | 49 |
| 135892 | Coding | 3 | 1250 | tgtggtcagagctgctacag | 87 | 50 |
| 135893 | Coding | 3 | 1293 | gtgtctcccattgtggagct | 71 | 51 |
| 135894 | Coding | 3 | 1302 | ctggaatctgtgtctcccat | 90 | 52 |
| 135895 | Coding | 3 | 1368 | tgtgaccgaaaggcacattc | 50 | 53 |
| 135896 | Coding | 3 | 1449 | ggcttcatcccagcatcagg | 84 | 54 |
| 135897 | Coding | 3 | 1453 | actgggcttcatcccagcat | 78 | 55 |
| 135898 | Stop Codon | 3 | 1465 | ccggcctggttaactgggct | 17 | 56 |
| 135899 | 3'UTR | 3 | 1512 | gtcatcctgccagggctcag | 90 | 57 |
| 135900 | 3'UTR | 3 | 1586 | agaggaacttggcccagaaa | 63 | 58 |
| 135901 | Intron | 17 | 1714 | ctaagcccagcagcccagct | 67 | 59 |
| 135902 | 3'UTR | 3 | 1926 | tgggtgactcaggcagcatc | 88 | 60 |
| 135903 | 3'UTR | 3 | 1963 | agtctcagcctcaggctgaa | 0 | 61 |
| 135904 | 3'UTR | 3 | 2022 | accccgttccctacagggct | 77 | 62 |
| 135905 | 3'UTR | 3 | 2037 | gagctaacttgaaggacccc | 76 | 63 |
| 135906 | Intron | 17 | 2354 | ttagctgtgccacactggga | 89 | 64 |
| 135907 | 3'UTR | 3 | 2453 | cagcactgaatatggtggcc | 82 | 65 |
| 135908 | 3'UTR | 3 | 2471 | gttatcttgcccaggccaca | 0 | 66 |
| 135909 | 3'UTR | 3 | 2472 | cgttatcttgcccaggccac | 83 | 67 |
| 135910 | 3'UTR | 3 | 2491 | agatttctagttagaagtgc | 43 | 68 |
| 135911 | 3'UTR | 3 | 2533 | gcttgttggcctgagtggta | 66 | 69 |
| 135912 | 3'UTR | 3 | 2563 | tgtggctggcagagtttggc | 60 | 70 |
| 135913 | 3'UTR | 3 | 2616 | gcaggcacaccggagtgaag | 71 | 71 |
| 135914 | 3'UTR | 3 | 2655 | tggtgtggcctaggacagca | 79 | 72 |
| 135915 | 3'UTR | 3 | 2671 | attccctgaaaggagatggt | 92 | 73 |
| 135916 | 3'UTR | 3 | 2732 | tctaggctgaggtaggagta | 92 | 74 |
| 135917 | 3'UTR | 3 | 2830 | ggccatgtaccaaagtggca | 92 | 75 |
| 135918 | 3'UTR | 3 | 2852 | gactggcacttgggatcaca | 99 | 76 |
| 135919 | 3'UTR | 3 | 3009 | ctacactggtttcccctctg | 77 | 77 |
| 135920 | 3'UTR | 3 | 3103 | gacaatttcatgccttctcc | 96 | 78 |
| 135921 | 3'UTR | 3 | 3202 | tggtaatggctgggctctcc | 81 | 79 |
| 135922 | 3'UTR | 3 | 3245 | tctgacatcttgattccagg | 69 | 80 |
| 135923 | 3'UTR | 3 | 3428 | gcagaaacctggccagtccc | 65 | 81 |
| 135924 | 3'UTR | 3 | 3439 | gtccaatgtgggcagaaacc | 88 | 82 |
| 135925 | 3'UTR | 3 | 3493 | tctcccaggactgtccacca | 98 | 83 |
| 135926 | 3'UTR | 3 | 3527 | ggctctgccctgtgatgcca | 95 | 84 |
| 135927 | 3'UTR | 3 | 3544 | caaattcatcgcttcccggc | 95 | 85 |
| 135928 | 3'UTR | 3 | 3651 | aaacaggtttattgataagc | 11 | 86 |
| 135929 | Intron | 17 | 4477 | ctacagaggcaggtttgagt | 77 | 87 |
| 135930 | Intron | 17 | 5054 | agacagggttgtgctatgtt | 71 | 88 |
| 135931 | Intron | 17 | 5190 | tggcacaatcatagctgact | 92 | 89 |
| 135932 | Intron | 17 | 5388 | gatggctgaatatttgtaaa | 44 | 90 |
| 135933 | Intron | 17 | 5431 | agggagaataatagcctacc | 63 | 91 |
| 135934 | Intron | 17 | 6640 | agccttccataagtagaagc | 63 | 92 |
| 135935 | Intron | 17 | 7126 | ccaagttcatggtcattccc | 87 | 93 |
| 135936 | Intron | 17 | 8748 | tgaattgattaccaacattt | 94 | 94 |
| 135937 | Intron | 17 | 8875 | caccttgcctggccagacca | 88 | 95 |
| 135938 | Intron | 17 | 8901 | gaagtactgagattacaggc | 84 | 96 |
| 135939 | Intron | 17 | 13529 | gtccccaggagggcagagcc | 51 | 97 |

As shown in Table 1, SEQ ID NOs 20, 21, 23, 24, 25, 26, 27, 28, 29, 30, 31, 32, 34, 36, 39, 40, 41, 43, 45, 46, 48, 49, 50, 51, 52, 53, 54, 55, 57, 58, 59, 60, 62, 63, 64, 65, 67, 68, 69, 70, 71, 72, 73, 74, 75, 76, 77, 78, 79, 80, 81, 82, 83, 84, 85, 87, 88, 89, 90, 91, 92, 93, 94, 95, 96 and 97 demonstrated at least 40% inhibition of human Tumor Necrosis Factor Receptor 2 expression in this assay and are therefore preferred. The target sites to which these preferred sequences

Example 16
Antisense Inhibition of Mouse Tumor Necrosis Factor Receptor 2 Expression by Chimeric Phosphorothioate Oligonucleotides Having 2'-MOE Wings and a Deoxy Gap In accordance with the present invention, a second series of oligonucleotides were designed to target different regions of the mouse Tumor Necrosis Factor Receptor 2 RNA, using published sequences (GenBank accession number M59378, incorporated herein as SEQ ID NO: 10, GenBank accession number Y14619, incorporated herein as SEQ ID NO: 98, and GenBank accession number Y14620, incorporated herein as SEQ ID NO: 99). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-doexynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse Tumor Necrosis Factor Receptor 2 mRNA levels by quantitative real-time PCR as described in other examples herein. Data are averages from two experiments. If present, "N.D." indicates "no data".

TABLE 2

Inhibition of mouse Tumor Necrosis Factor Receptor 2 mRNA levels by chimeric phosphorothioate oligonucieotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 135890 | Coding | 10 | 1189 | acgttcacgatgcaggtgac | 79 | 48 |
| 135891 | Coding | 10 | 1205 | gtcagagctgctacagacgt | 80 | 49 |
| 135892 | Coding | 10 | 1209 | tgtggtcagagctgctacag | 65 | 50 |
| 135942 | 5'UTR | 10 | 1 | cttgtgcctggagctctagt | 85 | 100 |
| 135943 | Coding | 10 | 70 | agctgcagttcgaagaccag | 73 | 101 |
| 135944 | Coding | 10 | 71 | cagctgcagttcgaagacca | 78 | 102 |
| 135945 | Coding | 10 | 118 | tagggtgtcaagacaacctg | 43 | 103 |
| 135946 | Coding | 10 | 123 | gtttgtagggtgtcaagaca | 77 | 104 |
| 135947 | Coding | 10 | 136 | tacccaggttccggtttgta | 93 | 105 |
| 135948 | Coding | 10 | 201 | gaggacacttagcacagcac | 88 | 106 |
| 135949 | Coding | 10 | 214 | acatattggccaggaggaca | 71 | 107 |
| 135950 | Coding | 10 | 316 | ctgcagctcaaacatgtacg | 46 | 108 |
| 135951 | Coding | 10 | 343 | tccacctggtcagtggtaca | 81 | 109 |
| 135952 | Coding | 10 | 424 | ccagaatgggttttcaaggc | 90 | 110 |
| 135953 | Coding | 10 | 467 | gccagggccgcacttgctca | 95 | 111 |
| 135954 | Coding | 10 | 487 | cttgaactggccactccgaa | 90 | 112 |
| 135955 | Coding | 10 | 550 | gatgtggtgtcagagaacgt | 84 | 113 |
| 135956 | Coding | 10 | 556 | gtggatgatgtggtgtcaga | 86 | 114 |
| 135957 | Coding | 10 | 590 | gatgctacagatgcggtggg | 24 | 115 |
| 135958 | Coding | 10 | 601 | ggaatagccaggatgctaca | 31 | 116 |
| 135959 | Coding | 10 | 622 | gcatctgtgcttgcatttcc | 62 | 117 |
| 135960 | Coding | 10 | 689 | ctctggctgagatacgtaga | 87 | 118 |
| 135961 | Coding | 10 | 695 | tgtgggctctggctgagata | 95 | 119 |
| 135962 | Coding | 10 | 701 | ggatcttgtgggctctggct | 85 | 120 |
| 135963 | Coding | 10 | 810 | ttgaagagagatgccaccc | 64 | 121 |
| 135964 | Coding | 10 | 816 | gaccaattggaagagagatg | 72 | 122 |
| 135965 | Coding | 10 | 822 | caatcagaccaattggaaga | 61 | 123 |
| 135966 | Coding | 10 | 823 | acaatcagaccaattggaag | 32 | 124 |
| 135967 | Coding | 10 | 856 | cctaacatcagcagacccag | 5 | 125 |
| 135968 | Coding | 10 | 890 | tttcctctgcaccaggatga | 85 | 126 |
| 135969 | Coding | 10 | 896 | cttctttttcctctgcacca | 61 | 127 |
| 135970 | Coding | 10 | 901 | gagggcttctttttcctctg | 55 | 128 |
| 135971 | Coding | 10 | 902 | ggagggcttctttttcctct | 48 | 129 |
| 135972 | Coding | 10 | 909 | gtaggcaggagggcttcttt | 29 | 130 |
| 135973 | Coding | 10 | 935 | cacatgaggcaccttggcat | 21 | 131 |
| 135974 | Coding | 10 | 937 | ggcacatgaggcaccttggc | 75 | 132 |
| 135975 | Coding | 10 | 1016 | ggagctgctgctggaactgg | 69 | 133 |
| 135976 | Coding | 10 | 1144 | tgggaagaatctgaaatcct | 36 | 134 |
| 135977 | Stop Codon | 10 | 1451 | gggtcaggccactttgactg | 51 | 135 |
| 135978 | 3'UTR | 10 | 1726 | tagctccttagaaggaaaaa | 91 | 136 |
| 135979 | 3'UTR | 10 | 1778 | tgcagtgtcagcattcaggc | 75 | 137 |
| 135980 | 3'UTR | 10 | 1807 | ccacttgctcctacttgctg | 85 | 138 |
| 135981 | 3'UTR | 10 | 1867 | agagggtacttcctaagagt | 82 | 139 |
| 135982 | 3'UTR | 10 | 1901 | gattcttgcatcaaaagaat | 80 | 140 |
| 135983 | 3'UTR | 10 | 1936 | cctataacagagcaactctg | 59 | 141 |
| 135984 | 3'UTR | 10 | 2004 | gtgttgctgaggatcaaacc | 68 | 142 |
| 135985 | 3'UTR | 10 | 2137 | tcattagaaggtcaggagga | 61 | 143 |
| 135986 | 3'UTR | 10 | 2162 | aaggaaggcgtggccttgga | 89 | 144 |
| 135987 | 3'UTR | 10 | 2313 | actcacagtgcctaacccgg | 93 | 145 |
| 135988 | 3'UTR | 10 | 2321 | ctgttccaactcacagtgcc | 74 | 146 |

TABLE 2-continued

Inhibition of mouse Tumor Necrosis Factor Receptor 2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 135989 | 3'UTR | 10 | 2371 | agagctggcttcagctgttt | 85 | 147 |
| 135990 | 3'UTR | 10 | 2389 | catgaatcctttggcaaaag | 80 | 148 |
| 135991 | 3'UTR | 10 | 2521 | ctgccaagttcatatccagt | 76 | 149 |
| 135992 | 3'UTR | 10 | 2578 | tatcttgattccagagtgct | 85 | 150 |
| 135993 | 3'UTR | 10 | 2609 | gagccttaacaagtcggccc | 69 | 151 |
| 135994 | 3'UTR | 10 | 2620 | ctgatgctgcagagccttaa | 73 | 152 |
| 135995 | 3'UTR | 10 | 2774 | tccttagcacacccttagg | 72 | 153 |
| 135996 | 3'UTR | 10 | 2815 | atttataagcaggaattctg | 69 | 154 |
| 135997 | 3'UTR | 10 | 3253 | cacatacatgcaaacatgga | 63 | 155 |
| 135998 | 3'UTR | 10 | 3314 | agtaactggagagtgatcaa | 70 | 156 |
| 135999 | 3'UTR | 10 | 3323 | gcccgcctcagtaactggag | 41 | 157 |
| 136000 | 3'UTR | 10 | 3346 | gcaagctctgggtacagatg | 58 | 158 |
| 136001 | 3'UTR | 10 | 3398 | agcactccataggcagacag | 78 | 159 |
| 136002 | 3'UTR | 10 | 3417 | gcagcctgcctgtaacctga | 82 | 160 |
| 136003 | 3'UTR | 10 | 3436 | taaatgtcgggcaggtatgg | 44 | 161 |
| 136004 | 3'UTR | 10 | 3489 | aaaatgcaggtatacaagtg | 62 | 162 |
| 136005 | 3'VTR | 10 | 3560 | gccatcttgccagttcaaaa | 95 | 163 |
| 136006 | 3'UTR | 10 | 3697 | tgatgtgtgcacatatgcag | 71 | 164 |
| 136007 | 3'UTR | 10 | 3731 | acatttatggtatgtgagtg | 80 | 165 |
| 136008 | Intron | 98 | 698 | gtccaatccagtgaagaatg | 0 | 166 |
| 136009 | Intron | 98 | 902 | tgatcagtacatgccttta | 59 | 167 |
| 136010 | Intron | 98 | 2592 | agtcaagtacactagttctt | 34 | 168 |
| 136011 | Intron | 98 | 3230 | agtccataagccccacagta | 25 | 169 |
| 136012 | Intron | 98 | 3690 | agtttagttaccttcaaagt | 0 | 170 |
| 136013 | Intron | 98 | 4366 | tggattctgcccagtgggtc | 60 | 171 |
| 136014 | Intron | 98 | 4524 | caaaacctcaaccctgaaga | 0 | 172 |
| 136015 | Intron | 99 | 599 | gaggaggcttcctggcagag | 72 | 173 |
| 136016 | Intron | 99 | 723 | acatcaatataggccagccg | 62 | 174 |

As shown in Table 2, SEQ ID NOs 48, 49, 50, 100, 101, 102, 103, 104, 105, 106, 107, 108, 109, 110, 111, 112, 113, 114, 117, 118, 119, 120, 121, 122, 123, 126, 127, 128, 129, 132, 133, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 167, 171, 173 and 174 demonstrated at least 40% inhibition of mouse Tumor Necrosis Factor Receptor 2 expression in this experiment and are therefore preferred. The target sites to which these preferred sequences are complementary are herein referred to as "active sites" and are therefore preferred sites for targeting by compounds of the present invention.

Example 17

Western Blot Analysis of Tumor Necrosis Factor Receptor 2 Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to Tumor Necrosis Factor Receptor 2 is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 8 to 30 nucleobases in length targeted to nucleobases 198 through 1472 of a coding region, or nucleobases 1512 through 3671 of a 3'-untranslated region of a nucleic acid molecule encoding a human Tumor Necrosis Factor Receptor 2 (SEQ ID NO: 3), or nucleobases 4477 through 8921 of an intron region encoding human Tumor Necrosis Factor Receptor 2 (SEQ ID NO: 17), or nucleobases 70–1164 of a coding region or nucleobases 1726–3751 of a 3'-untranslated region of a nucleic acid molecule encoding a mouse Tumor Necrosis Factor Receptor 2 (SEQ ID NO: 10), or nucleobases 698–743 of an intron region of a nucleic acid molecule encoding murine Tumor Necrosis Factor Receptor 2 (SEQ ID NO:98), wherein said compound specifically hybridizes with one or said regions and inhibits the expression of Tumor Necrosis Factor Receptor 2.

2. The compound of claim 1 which is an antisense oligonucleotide.

3. A compound up to 50 nucleobases in length comprising at least an 8-nucleobases portion of SEQ ID NO: 20, 21 23, 24, 25, 26, 27, 28, 29, 30, 31, 32, 34, 36, 39, 40, 41, 43, 45, 46, 48, 49, 50, 51, 52, 53, 54, 55, 57, 58, 59, 60, 62, 63, 64, 65, 67, 68, 69, 70, 71, 72, 73, 74, 75, 76, 77, 78, 79, 80, 81, 82, 83, 84, 85, 87, 88, 89, 90, 91, 92, 93, 94, 95, 96, 97, 100, 101, 102, 103, 104, 105, 106, 107, 108, 109, 110, 111, 112, 113, 114, 117, 118, 119, 120, 121, 122, 123, 126, 127, 128, 129, 132, 133, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 167, 171, 173 or 174 which inhibits the expression of human or mouse Tumor Necrosis Factor Receptor 2.

4. The compound of claim 2 wherein the antisense oligonucleotide comprises at least one modified internucleoside linkage.

5. The compound of claim 4 wherein the modified internucleoside linkage is a phosphorothioate linkage.

6. The compound of claim 2 wherein the antisense oligonucleotide comprises at least one modified sugar moiety.

7. The compound of claim 6 wherein the modified sugar moiety is a 2'-O-methoxyethyl sugar moiety.

8. The compound of claim 2 wherein the antisense oligonucleotide comprises at least one modified nucleobase.

9. The compound of claim 8 wherein the modified nucleobase is a 5-methylcytosine.

10. The compound of claim 2 wherein the antisense oligonucleotide is a chimeric oligonucleotide.

11. A composition comprising the compound of claim 1 and a pharmaceutically acceptable carrier or diluent.

12. The composition of claim 11 further comprising a colloidal dispersion system.

13. The composition of claim 11 wherein the compound is an antisense oligonucleotide.

14. A method of inhibiting the expression of human or mouse Tumor Necrosis Factor Receptor 2 in cells or tissues comprising contacting said cells or tissues in vitro with the compound of claim 1 so that expression of human or mouse Tumor Necrosis Factor Receptor 2 is inhibited.

15. The compound of claim 3 which is an antisense oligonucleotide.

16. The compound of claim 15 wherein the antisense oligonucleotide comprises at least one modified internucleoside linkage.

17. The compound of claim 16 wherein the modified internucleoside linkage is a phosphorothioate linkage.

18. The compound of claim 15 wherein the antisense oligonucleotide comprises at least one modified sugar moiety.

19. The compound of claim 18 wherein the modified sugar moiety is a 2'-O-methoxyethyl sugar moiety.

20. The compound of claim 15 wherein the antisense oligonucleotide comprises at least one modified nucleobase.

21. The compound of claim 20 wherein the modified nucleobase is a 5-methylcytosine.

22. The compound of claim 15 wherein the antisense oligonucleotide is a chimeric oligonucleotide.

23. A composition comprising the compound of claim 3 and a pharmaceutically acceptable carrier or diluent.

24. The composition of claim 23 further comprising a colloidal dispersion system.

25. The composition of claim 23 wherein the compound is an antisense oligonucleotide.

26. A method of inhibiting the expression of human or murine Tumor Necrosis Factor Receptor 2 in cells or tissues comprising contacting said cells or tissues in vitro with the compound of claim 3 so that expression of human or murine Tumor Necrosis Factor Receptor 2 is inhibited.

* * * * *

SEQUENCE LISTING

<160> NUMBER OF SEQ ID NOS: 174

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg          20

```
<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                                    20

<210> SEQ ID NO 3
<211> LENGTH: 3683
<212> TYPE: DNA
<213> ORGANISM: Homo sapiens
<220> FEATURE:
<221> NAME/KEY: CDS
<222> LOCATION: (90)...(1475)

<400> SEQUENCE: 3
gcgagcgcag cggagcctgg agagaaggcg ctgggctgcg agggcgcgag g gcgcgaggg       60 caggggcaa ccggaccccg cccgcaccc atg gcg ccc gtc gc c gtc tgg gcc        113
                                 Met Ala Pro Val Ala Val Trp Ala
                                   1               5
gcg ctg gcc gtc gga ctg gag ctc tgg gct g cg gcg cac gcc ttg ccc        161
Ala Leu Ala Val Gly Leu Glu Leu Trp Ala A la Ala His Ala Leu Pro
     10              15                   20 gcc cag gtg gca ttt aca ccc tac gcc ccg g ag ccc ggg agc aca tgc        209
Ala Gln Val Ala Phe Thr Pro Tyr Ala Pro G lu Pro Gly Ser Thr Cys
 25              30              35                  40 cgg ctc aga gaa tac tat gac cag aca gct c ag atg tgc tgc agc aaa        257
Arg Leu Arg Glu Tyr Tyr Asp Gln Thr Ala G ln Met Cys Cys Ser Lys
             45                  50                  55 tgc tcg ccg ggc caa cat gca aaa gtc ttc t gt acc aag acc tcg gac        305
Cys Ser Pro Gly Gln His Ala Lys Val Phe C ys Thr Lys Thr Ser Asp
         60                  65                  70 acc gtg tgt gac tcc tgt gag gac agc aca t ac acc cag ctc tgg aac        353
Thr Val Cys Asp Ser Cys Glu Asp Ser Thr T yr Thr Gln Leu Trp Asn
     75                  80                  85 tgg gtt ccc gag tgc ttg agc tgt ggc tcc c gc tgt agc tct gac cag        401
Trp Val Pro Glu Cys Leu Ser Cys Gly Ser A rg Cys Ser Ser Asp Gln
 90                  95                 100 gtg gaa act caa gcc tgc act cgg gaa cag a ac cgc atc tgc acc tgc        449
Val Glu Thr Gln Ala Cys Thr Arg Glu Gln A sn Arg Ile Cys Thr Cys
105             110             115                 120 agg ccc ggc tgg tac tgc gcg ctg agc aag c ag gag ggg tgc cgg ctg        497
Arg Pro Gly Trp Tyr Cys Ala Leu Ser Lys G ln Glu Gly Cys Arg Leu
            125             130                 135 tgc gcg ccg ctg cgc aag tgc cgc ccg ggc t tc ggc gtg gcc aga cca        545
Cys Ala Pro Leu Arg Lys Cys Arg Pro Gly P he Gly Val Ala Arg Pro
        140             145                 150 gga act gaa aca tca gac gtg gtg tgc aag c cc tgt gcc ccg ggg acg        593
Gly Thr Glu Thr Ser Asp Val Val Cys Lys P ro Cys Ala Pro Gly Thr
    155             160                 165 ttc tcc aac acg act tca tcc acg gat att t gc agg ccc cac cag atc        641
Phe Ser Asn Thr Thr Ser Ser Thr Asp Ile C ys Arg Pro His Gln Ile
170             175                 180 tgt aac gtg gtg gcc atc cct ggg aat gca a gc atg gat gca gtc tgc        689
Cys Asn Val Val Ala Ile Pro Gly Asn Ala S er Met Asp Ala Val Cys
185             190             195                 200 acg tcc acg tcc ccc acc cgg agt atg gcc c ca ggg gca gta cac tta        737
Thr Ser Thr Ser Pro Thr Arg Ser Met Ala P ro Gly Ala Val His Leu
        205             210                 215
```

|  |  |
|---|---|
| ccc cag cca gtg tcc aca cga tcc caa cac a cg cag cca act cca gaa<br>Pro Gln Pro Val Ser Thr Arg Ser Gln His T hr Gln Pro Thr Pro Glu<br>220                    225                    230 | 785 |
| ccc agc act gct cca agc acc tcc ttc ctg c tc cca atg ggc ccc agc<br>Pro Ser Thr Ala Pro Ser Thr Ser Phe Leu L eu Pro Met Gly Pro Ser<br>235                    240                    245 | 833 |
| ccc cca gct gaa ggg agc act ggc gac ttc g ct ctt cca gtt gga ctg<br>Pro Pro Ala Glu Gly Ser Thr Gly Asp Phe A la Leu Pro Val Gly Leu<br>250                    255                    260 | 881 |
| att gtg ggt gtg aca gcc ttg ggt cta cta a ta ata gga gtg gtg aac<br>Ile Val Gly Val Thr Ala Leu Gly Leu Leu I le Ile Gly Val Val Asn<br>265                    270                    275                    280 | 929 |
| tgt gtc atc atg acc cag gtg aaa aag aag c cc ttg tgc ctg cag aga<br>Cys Val Ile Met Thr Gln Val Lys Lys Lys P ro Leu Cys Leu Gln Arg<br>285                    290                    295 | 977 |
| gaa gcc aag gtg cct cac ttg cct gcc gat a ag gcc cgg ggt aca cag<br>Glu Ala Lys Val Pro His Leu Pro Ala Asp L ys Ala Arg Gly Thr Gln<br>300                    305                    310 | 1025 |
| ggc ccc gag cag cag cac ctg ctg atc aca g cg ccg agc tcc agc agc<br>Gly Pro Glu Gln Gln His Leu Leu Ile Thr A la Pro Ser Ser Ser Ser<br>315                    320                    325 | 1073 |
| agc tcc ctg gag agc tcg gcc agt gcg ttg g ac aga agg gcg ccc act<br>Ser Ser Leu Glu Ser Ser Ala Ser Ala Leu A sp Arg Arg Ala Pro Thr<br>330                    335                    340 | 1121 |
| cgg aac cag cca cag gca cca ggc gtg gag g cc agt ggg gcc ggg gag<br>Arg Asn Gln Pro Gln Ala Pro Gly Val Glu A la Ser Gly Ala Gly Glu<br>345                    350                    355                    360 | 1169 |
| gcc cgg gcc agc acc ggg agc tca gat tct t cc cct ggt ggc cat ggg<br>Ala Arg Ala Ser Thr Gly Ser Ser Asp Ser S er Pro Gly Gly His Gly<br>365                    370                    375 | 1217 |
| acc cag gtc aat gtc acc tgc atc gtg aac g tc tgt agc agc tct gac<br>Thr Gln Val Asn Val Thr Cys Ile Val Asn V al Cys Ser Ser Ser Asp<br>380                    385                    390 | 1265 |
| cac agc tca cag tgc tcc tcc caa gcc agc t cc aca atg gga gac aca<br>His Ser Ser Gln Cys Ser Ser Gln Ala Ser S er Thr Met Gly Asp Thr<br>395                    400                    405 | 1313 |
| gat tcc agc ccc tcg gag tcc ccg aag gac g ag cag gtc ccc ttc tcc<br>Asp Ser Ser Pro Ser Glu Ser Pro Lys Asp G lu Gln Val Pro Phe Ser<br>410                    415                    420 | 1361 |
| aag gag gaa tgt gcc ttt cgg tca cag ctg g ag acg cca gag acc ctg<br>Lys Glu Glu Cys Ala Phe Arg Ser Gln Leu G lu Thr Pro Glu Thr Leu<br>425                    430                    435                    440 | 1409 |
| ctg ggg agc acc gaa gag aag ccc ctg ccc c tt gga gtg cct gat gct<br>Leu Gly Ser Thr Glu Glu Lys Pro Leu Pro L eu Gly Val Pro Asp Ala<br>445                    450                    455 | 1457 |
| ggg atg aag ccc agt taa ccaggccggt gtgggctgtg t cgtagccaa<br>Gly Met Lys Pro Ser  *<br>460 | 1505 |
| ggtgggctga gccctggcag gatgaccctg cgaagggcc ctggtccttc c aggccccca | 1565 |
| ccactaggac tctgaggctc tttctgggcc aagttcctct agtgccctcc a cagccgcag | 1625 |
| cctccctctg acctgcaggc caagagcaga ggcagcgagt tggggaaagc c tctgctgcc | 1685 |
| atggtgtgtc cctctcggaa ggctggctgg gcatggacgt tcgggcatg c tggggcaag | 1745 |
| tccctgactc tctgtgacct gccccgccca gctgcacctg ccagcctggc t tctggagcc | 1805 |
| cttgggtttt tgtttgttt gtttgtttgt tgtttgttt ctcccccctgg g ctctgccca | 1865 |
| gctctggctt ccagaaaacc ccagcatcct tttctgcaga ggggctttct g gagaggagg | 1925 |
| gatgctgcct gagtcaccca tgaagacagg acagtgcttc agcctgaggc t gagactgcg | 1985 |

-continued

```
ggatggtcct ggggctctgt gtagggagga ggtggcagcc ctgtagggaa c gggtccttt    2045 caagttagct caggaggctt ggaaagcatc acctcaggcc aggtgcagtg g ctcacgcct    2105 atgatcccag cactttggga ggctgaggcg ggtggatcac ctgaggttag g agttcgaga    2165 ccagcctggc caacatggta aaaccccatc tctactaaaa atacagaaat t agccgggcg    2225 tggtggcggg cacctatagt cccagctact cagaagcctg aggctgggaa a tcgtttgaa    2285 cccgggaagc ggaggttgca gggagccgag atcacgccac tgcactccag c ctgggcgac    2345 agagcgagag tctgtctcaa aagaaaaaaa aaaagcacc gcctccaaat g ctaacttgt    2405 cctttgtac catggtgtga aagtcagatg cccagagggc ccaggcaggc c accatattc    2465 agtgctgtgg cctgggcaag ataacgcact tctaactaga aatctgccaa t tttttaaaa    2525 aagtaagtac cactcaggcc aacaagccaa cgacaaagcc aaactctgcc a gccacatcc    2585 aaccccccac ctgccatttg caccctccgc cttcactccg gtgtgcctgc a gccccgcgc    2645 ctccttcctt gctgtcctag gccacaccat ctccttcag g gaatttcag g aactagaga    2705 tgactgagtc ctcgtagcca tctctctact cctacctcag cctagaccct c ctcctcccc    2765 cagaggggtg ggttcctctt ccccactccc caccttcaat tcctgggccc c aaacgggct    2825 gccctgccac tttggtacat ggccagtgtg atcccaagtg ccagtcttgt g tctgcgtct    2885 gtgttgcgtg tcgtgggtgt gtgtagccaa ggtcggtaag ttgaatggcc t gccttgaag    2945 ccactgaagc tgggattcct ccccattaga gtcagccttc ccctcccag g gccagggcc    3005 ctgcagaggg gaaaccagtg tagccttgcc cggattctgg gaggaagcag g ttgaggggc    3065 tcctggaaag gctcagtctc aggagcatgg ggataaagga gaaggcatga a attgtctag    3125 cagagcaggg gcagggtgat aaattgttga taaattccac tggacttgag c ttggcagct    3185 gaactattgg agggtgggag agcccagcca ttaccatgga gacaagaagg g ttttccacc    3245 ctggaatcaa gatgtcagac tggctggctg cagtgacgtg cacctgtact c aggaggctg    3305 aggggaggat cactggagcc caggagtttg aggctgcagc gagctatgat c gcgccacta    3365 cactccagcc tgagcaacag agtgagaccc tgtctcttaa agaaaaaaaa a gtcagactg    3425 ctgggactgg ccaggtttct gcccacattg gacccacatg aggacatgat g gagcgcacc    3485 tgccccctgg tggacagtcc tgggagaacc tcaggcttcc ttggcatcac a gggcagagc    3545 cgggaagcga tgaatttgga gactctgtgg ggccttggtt cccttgtgtg t gtgtgttga    3605 tcccaagaca atgaaagttt gcactgtatg ctggacggca ttcctgctta t caataaacc    3665 tgtttgtttt aaaaaaaa                                                   3683
```

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4 cactcccac cttcaattcc t                                                21

<210> SEQ ID NO 5
<211> LENGTH: 22
<212> TYPE: DNA
<213> ORGANISM: Artificial Sequence
<220> FEATURE:
<223> OTHER INFORMATION: PCR Primer

```
<400> SEQUENCE: 5
gcagacacaa gactggcact tg                                              22

<210> SEQ ID NO 6
<211> LENGTH: 19
<212> TYPE: DNA
<213> ORGANISM: Artificial Sequence
<220> FEATURE:
<223> OTHER INFORMATION: PCR Probe

<400> SEQUENCE: 6
cccaaacggg ctgccctgc                                                  19

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                  19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                 20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                 20

<210> SEQ ID NO 10
<211> LENGTH: 3796
<212> TYPE: DNA
<213> ORGANISM: Mus musculus
<220> FEATURE:
<221> NAME/KEY: CDS
<222> LOCATION: (43)...(1467)

<400> SEQUENCE: 10
actagagctc caggcacaag ggcgggagcc accgctgccc ct atg gc g ccc gcc        54
                                              Met Ala Pro Ala
                                                1
gcc ctc tgg gtc gcg ctg gtc ttc gaa ctg c ag ctg tgg gcc acc ggg      102
Ala Leu Trp Val Ala Leu Val Phe Glu Leu G ln Leu Trp Ala Thr Gly
  5                  10              15                  20 cac aca gtg ccc gcc cag gtt gtc ttg aca c cc tac aaa ccg gaa cct      150
His Thr Val Pro Ala Gln Val Val Leu Thr P ro Tyr Lys Pro Glu Pro
             25                  30                  35 ggg tac gag tgc cag atc tca cag gaa tac t at gac agg aag gct cag      198
Gly Tyr Glu Cys Gln Ile Ser Gln Glu Tyr T yr Asp Arg Lys Ala Gln
         40                  45                  50 atg tgc tgt gct aag tgt cct cct ggc caa t at gtg aaa cat ttc tgc      246
```

```
                                                    -continued

Met Cys Cys Ala Lys Cys Pro Gly Gln Tyr Val Lys His Phe Cys
         55                  60                  65 aac aag acc tcg gac acc gtg tgt gcg gac tgt gag gca agc atg tat      294
Asn Lys Thr Ser Asp Thr Val Cys Ala Asp Cys Glu Ala Ser Met Tyr
     70                  75                  80 acc cag gtc tgg aac cag ttt cgt aca tgt ttg agc tgc agt tct tcc      342
Thr Gln Val Trp Asn Gln Phe Arg Thr Cys Leu Ser Cys Ser Ser Ser
 85                  90                  95                 100 tgt acc act gac cag gtg gag atc cgc gcc tgc act aaa cag cag aac      390
Cys Thr Thr Asp Gln Val Glu Ile Arg Ala Cys Thr Lys Gln Gln Asn
                105                 110                 115 cga gtg tgt gct tgc gaa gct ggc agg tac tgc gcc ttg aaa acc cat      438
Arg Val Cys Ala Cys Glu Ala Gly Arg Tyr Cys Ala Leu Lys Thr His
            120                 125                 130 tct ggc agc tgt cga cag tgc atg agg ctg agc aag tgc ggc cct ggc      486
Ser Gly Ser Cys Arg Gln Cys Met Arg Leu Ser Lys Cys Gly Pro Gly
        135                 140                 145 ttc gga gtg gcc agt tca aga gcc cca aat gga aat gtg cta tgc aag      534
Phe Gly Val Ala Ser Ser Arg Ala Pro Asn Gly Asn Val Leu Cys Lys
    150                 155                 160 gcc tgt gcc cca ggg acg ttc tct gac acc aca tca tcc act gat gtg      582
Ala Cys Ala Pro Gly Thr Phe Ser Asp Thr Thr Ser Ser Thr Asp Val
165                 170                 175                 180 tgc agg ccc cac cgc atc tgt agc atc ctg gct att ccc gga aat gca      630
Cys Arg Pro His Arg Ile Cys Ser Ile Leu Ala Ile Pro Gly Asn Ala
                185                 190                 195 agc aca gat gca gtc tgt gcg ccc gag tcc cca act cta agt gcc atc      678
Ser Thr Asp Ala Val Cys Ala Pro Glu Ser Pro Thr Leu Ser Ala Ile
            200                 205                 210 cca agg aca ctc tac gta tct cag cca gag ccc aca aga tcc caa ccc      726
Pro Arg Thr Leu Tyr Val Ser Gln Pro Glu Pro Thr Arg Ser Gln Pro
        215                 220                 225 ctg gat caa gag cca ggg ccc agc caa act cca agc atc ctt aca tcg      774
Leu Asp Gln Glu Pro Gly Pro Ser Gln Thr Pro Ser Ile Leu Thr Ser
    230                 235                 240 ttg ggt tca acc ccc att att gaa caa agt acc aag ggt ggc atc tct      822
Leu Gly Ser Thr Pro Ile Ile Glu Gln Ser Thr Lys Gly Gly Ile Ser
245                 250                 255                 260 ctt cca att ggt ctg att gtt gga gtg aca tca ctg ggt ctg ctg atg      870
Leu Pro Ile Gly Leu Ile Val Gly Val Thr Ser Leu Gly Leu Leu Met
                265                 270                 275 tta gga ctg gtg aac tgc atc atc ctg gtg cag agg aaa aag aag ccc      918
Leu Gly Leu Val Asn Cys Ile Ile Leu Val Gln Arg Lys Lys Lys Pro
            280                 285                 290 tcc tgc cta caa aga gat gcc aag gtg cct cat gtg cct gat gag aaa      966
Ser Cys Leu Gln Arg Asp Ala Lys Val Pro His Val Pro Asp Glu Lys
        295                 300                 305 tcc cag gat gca gta ggc ctt gag cag cag cac ctg ttg acc aca gca     1014
Ser Gln Asp Ala Val Gly Leu Glu Gln Gln His Leu Leu Thr Thr Ala
    310                 315                 320 ccc agt tcc agc agc agc tcc cta gag agc tca gcc agc gct ggg gac     1062
Pro Ser Ser Ser Ser Ser Leu Glu Ser Ser Ala Ser Ala Gly Asp
325                 330                 335                 340 cga agg gcg ccc cct ggg ggc cat ccc caa gca aga gtc atg gcg gag     1110
Arg Arg Ala Pro Pro Gly Gly His Pro Gln Ala Arg Val Met Ala Glu
                345                 350                 355 gcc caa ggg ttt cag gag gcc cgt gcc agc tcc agg att tca gat tct     1158
Ala Gln Gly Phe Gln Glu Ala Arg Ala Ser Ser Arg Ile Ser Asp Ser
            360                 365                 370
```

-continued

```
tcc cac gga agc cac ggg acc cac gtc aac g tc acc tgc atc gtg aac    1206
Ser His Gly Ser His Gly Thr His Val Asn V al Thr Cys Ile Val Asn
            375                 380                 385 gtc tgt agc agc tct gac cac agt tct cag t gc tct tcc caa gcc agc    1254
Val Cys Ser Ser Ser Asp His Ser Ser Gln C ys Ser Ser Gln Ala Ser
        390                 395                 400 gcc aca gtg gga gac cca gat gcc aag ccc t ca gcg tcc cca aag gat    1302
Ala Thr Val Gly Asp Pro Asp Ala Lys Pro S er Ala Ser Pro Lys Asp
405                 410                 415                 420 gag cag gtc ccc ttc tct cag gag gag tgt c cg tct cag tcc ccg tgt    1350
Glu Gln Val Pro Phe Ser Gln Glu Glu Cys P ro Ser Gln Ser Pro Cys
                425                 430                 435 gag act aca gag aca ctg cag agc cat gag a ag ccc ttg ccc ctt ggt    1398
Glu Thr Thr Glu Thr Leu Gln Ser His Glu L ys Pro Leu Pro Leu Gly
            440                 445                 450 gtg ccg gat atg ggc atg aag ccc agc caa g ct ggc tgg ttt gat cag    1446
Val Pro Asp Met Gly Met Lys Pro Ser Gln A la Gly Trp Phe Asp Gln
        455                 460                 465 att gca gtc aaa gtg gcc tga ccctgacag ggtaaca cc ctgcaaaggg         1497
Ile Ala Val Lys Val Ala
        470             475 acccccgaga ccctgaaccc atggaacttc atgactttg ctggatccat t tcccttagt   1557
ggcttccaga gccccagttg caggtcaagt gagggctgag acagctagag t ggtcaaaaa  1617
ctgccatggt gttttatggg ggcagtccca ggaagttgtt gctcttccat g acccctctg  1677
gatctcctgg gctcttgcct gattcttgct tctgagaggc cccagtattt t ttccttcta  1737
aggagctaac atcctcttcc atgaatagca cagctcttca gcctgaatgc t gacactgca  1797
gggcggttcc agcaagtagg agcaagtggt ggcctggtag ggcacagagg c ccttcaggt  1857
tagtgctaaa ctcttaggaa gtaccctctc caagcccacc gaaattcttt t gatgcaaga  1917
atcagaggcc ccatcaggca gagttgctct gttataggat ggtagggctg t aactcagtg  1977
gtccagtgtg cttttagcat gccctgggtt tgatcctcag caacacatgc a aaacgtaag  2037
tagacagcag acagcagaca gcacagccag cccctgtgt ggtttgcagc c tctgccttt   2097
gactttact ctggtgggca cacagagggc tggagctcct cctcctgacc t tctaatgag   2157
ccottccaag gccacgcctt ccttcaggga atctcaggga ctgtagagtt c ccaggcccc  2217
tgcagccacc tgtctcttcc tacctcagcc tggagcactc cctctaactc c ccaacggct  2277
tggtactgta cttgctgtga ccccaagtgc attgtccggg ttaggcactg t gagttggaa  2337
cagctgatga catcggttga aaggcccacc cggaaacagc tgaagccagc t cttttgcca  2397
aaggattcat gccggttttc taatcaacct gctcccctag catgcctgga a ggaaagggt  2457
tcaggagact cctcaagaag caagttcagt ctcaggtgct tggatgccat g ctcaccgat  2517
tccactggat atgaacttgg cagaggagcc tagttgttgc catggagact t aaagagctc  2577
agcactctgg aatcaagata ctggacactt ggggccgact tgttaaggct c tgcagcatc  2637
agactgtaga ggggaaggaa cacgtctgcc ccctggtggc ccgtcctggg a tgacctcgg  2697
gcctcctagg caacaaaaga atgaattgga aaggactgtt cctgggtgtg g cctagctcc  2757
tgtgcttgtg tggatcccta aagggtgtgc taaggagcaa ttgcactgtg t gctggacag  2817
aattcctgct tataaatgct ttttgttgtt gttttgtaca ctgagccctg g ctgagccac  2877
cccaccccac ctcccatccc acctttacag ccactcttgc agagaacctg g ctgtctccc  2937
acttgtagcc tgtggatgct gaggaaacac ccagccaagt agactccagg c ttccccta   2997
tctcctgctc tgagtctggc ctcctcattg tgttgtggga aggagacggg t tctgtcatc  3057
```

-continued

```
tcggaagccc acaccgtgga tgtgaacaat ggctgtacta gcttagacca g cttagggct     3117 ctgcaatcag aggaggggga gcagggaaca atttgagtgc tgacctataa c acattccta     3177 aaggatgggc agtccagaat ctccctcctt cagtgtgtgt gtgtgtgtgt g tgtgtgtgt     3237 gtgtgtgtgt gtgtgtccat gtttgcatgt atgtgtgtgc cagtgtgtgg a ggcccgagg     3297 ttggctttgg gtgtgtttga tcactctcca gttactgagg cgggctctca t ctgtaccca     3357 gagcttgcac attttctagt ctaacttgct tcagggatct ctgtctgcct a tggagtgct     3417 caggttacag gcaggctgcc atacctgccc gacatttaca tgaatactag a gatctgaat     3477 tctggtcctc acacttgtat acctgcattt tatccactaa gacatctctc c aagggctcc     3537 ccctcctat ttaataagtt agttttgaac tggcaagatg gctcagtggg t aaggcagtt      3597 tgcggacaaa cctgatgacc tgagttggat ccctgaccat aaggtagaag a gacctgatt     3657 cctgcaagtt gtcctctgac caccacccca tacatgcttc tgcatatgtg c acacatcac     3717 attcttgcac acacactcac ataccataaa tgtaataaat tttttttaaat a aattgattt    3777 tatcttttaa aaaaaaaa                                                    3796
```

<210> SEQ ID NO 11
<211> LENGTH: 20
<212> TYPE: DNA
<213> ORGANISM: Artificial Sequence
<220> FEATURE:
<223> OTHER INFORMATION: PCR Primer

<400> SEQUENCE: 11
gtttgcagcc tctgcctttg                                                  20

<210> SEQ ID NO 12
<211> LENGTH: 17
<212> TYPE: DNA
<213> ORGANISM: Artificial Sequence
<220> FEATURE:
<223> OTHER INFORMATION: PCR Primer

<400> SEQUENCE: 12
aaggcgtggc cttggaa                                                     17

<210> SEQ ID NO 13
<211> LENGTH: 29
<212> TYPE: DNA
<213> ORGANISM: Artificial Sequence
<220> FEATURE:
<223> OTHER INFORMATION: PCR Probe

<400> SEQUENCE: 13
agctcctcct cctgaccttc taatgagcc                                        29

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
ggcaaattca acggcacagt                                                  20

<210> SEQ ID NO 15
<211> LENGTH: 20
<212> TYPE: DNA

<213> ORGANISM: Artificial Sequence
<220> FEATURE:
<223> OTHER INFORMATION: PCR Primer

<400> SEQUENCE: 15
gggtctcgct cctggaagat                                                    20

<210> SEQ ID NO 16
<211> LENGTH: 27
<212> TYPE: DNA
<213> ORGANISM: Artificial Sequence
<220> FEATURE:
<223> OTHER INFORMATION: PCR Probe

<400> SEQUENCE: 16
aaggccgaga atgggaagct tgtcatc                                            27

<210> SEQ ID NO 17
<211> LENGTH: 15602
<212> TYPE: DNA
<213> ORGANISM: Homo sapiens
<220> FEATURE:

<400> SEQUENCE: 17
gatcttggct gggcacggtg gctcactcct gtaatcccag cactttggaa g gccgaggta      60
gatggatcac ttgaggtcag gagttcaaga ctagtctggc catcatggta a aaccccatc    120
tctactaaaa acagaaaaat tagccaggcg tggtggcacg tgcctgtagt c tcagctact   180
cgggaggctg aggcaggaga gtcgcttgaa cccgggcagt ggaggttgca a tgagctgag    240
atcacaccac tgctctccag cctgggcaat agagcaagac tccatctcaa a agaaaaaat   300
aaaataaaat aaataaataa aatatcttac ttagttgtgg gggctgtccc g tgctattca    360
gcagcatctt tggtctttat ttacttacat gccagcctca ttcccactcc a gtggtgaca    420
atcaaaaatt ctccagacat caccaagtgt cccctggagg gcaaaatcac c cctagtgga   480
gaaccactgc tcgagggaac agctcagccc tgggcagccc aatacccgaa g cttacacca    540
ggtgtttgga atcagataga ttgatttcat cccctgattt tggtgacaag a aaagagatg   600
cagggaggaa aactgagttg ctcaaggtcg caccgcagtg tgtctctgga c tcccatctc    660
agtgctcttt gccctgccct acagtatttc agtggggagg aaattttctc a ttccccggc    720
gagcgagttt cactgctccc tttctccagc ttcaattcag tgacactgac g gttgccgcc    780
tggtggcgtg cgtagagcag gtgtctcccc caagctcttc cgcagcagcc c agctgtcac    840
cttcccttc cccaccaagc gtttcccaat cctctgtgca ctgaagatgt c ctgggtgtg    900
gcctagcagc ctctgcttcc cttttccatt tttttttttct ttctttcttt t ttttttttt    960
gagacagcta tgtcgcccag gctgcagtgc agtggcgccc tcttggctca c tgcagcctc   1020
cgcctcccgg gttcgagtgg tcatcccacc tcagcctccc aagtagatgg g actatgggc   1080
atgcgccacc atgcctggct aatttttata ttttttagtag agacgggttt t gccatgtt   1140
ggccaggctg gtctcaaacc cctgacctca gtgatctgc ccacctcggt c tcccaaagt   1200
actgggatga gaggcataag ccaccacgcc tggcccttt cctttcactg t tgctctcag   1260
tgttcactga atgtgagtga ctcaagtatc tgttgagtgc cccagtggtg t gtctagtgc   1320
agaaaaaaac ccccaaaccc tgatttgtgg tgtttgctaa tttctgtggt a taaacactc   1380
acactgtagc cagtttccaa ctcccaagac cttcctgaat atggagttgg g aggaaatct   1440
gcacaggcct gagcttatcc cagcacagcc ctggctgagc cctgccaggc t ctttgtgac   1500

-continued

```
tgagtcccca cgcatccctg tggggcaggg agcatcatca ccccatttt a cagaggagg        1560 aaactgagac tctgggaggt tccatttttc ctgtaggatt agatcattag g tgagtggca       1620 tagcccaggt ttgaatcagg tttatgcctg tgtcccacgc tactcctcaa c cagcagcta      1680 ctcctgataa gaggccagtg gagagtcctc ttgagctggg ctgctgggct t agagtgtgg      1740 actcagcacc cacctgctcc tcctgccaca gaaagaacgt ccagggcatg g gagacagtg     1800 gcgttccttt gtttagaaaa caccaacatg tggccgggcg ccatggctca c gcctgtaat     1860 cccagcactt tgggaggccg agggggcgg atcacgaggt caggagatcg a gaccatcct      1920 ggctaacaca gtgaaacccc atctctacta aaataaaaa aaattagccg g gcgtggtgg       1980 cgggcgcccg tagtcccagc tactccgag gctgaggcag aatagcgtga a cccgggagg      2040 tggagcttgc agtgtactga gatcgcacca ctgcactcca gcctgggcga t agagcgaga    2100 ctccatctca aaaaaaaaaa aaaaaaaac caatatgtga gcttacccac a atcaccccc      2160 atggacacgg acacactcat gcacggaccc acgtctgata acaggtgcga a catttatcg   2220 ggtgttgaac ggatgccagg cactgtgccc agcgttcttt attctcacag c catgctgcc    2280 acacgcaggc agtatgattc ttgtccccca ttatatggcc caagaatcat g ggcccagag    2340 aagttagtaa cttteccagt gtggcacagc taatgatcac ggcctgggac a cgaacctag  2400 gagtgtctct cctcgccacc ccagcgcaca cactcactac gtcactcaca g atatgcaca  2460 catgccccca acatagacac acgtgtgcac gcttcacacc ctcacgcctg t agacacagg  2520 tgtgtgagcc ttgtgaacac acaaacagac ggacacagca ggaacctgga g gacctggcc    2580 cgtggctctg ctgggtctct gcttctgccc agcagggctg ggccaggagg g gccgggagc   2640 tgagggtgct ggctggctgg ctgctggct ggaattctgt tttttttttt t ttttttgaga   2700 aagagtcttg ctttgtcgcc caggctggag tgcagtggca caatcttggc t cactgcaag  2760 ctccgcctcc cggttcaca ccattctcct gcctcagcct cccaagtagc t gggactaca   2820 ggcacccacc agctcgccca gctaatttt tgtatttta gtagagacgg g gtttcacct    2880 tgttagccag gatggtctca atctcctgac ctcgtgattc ggtgaccacc t cggcctccc    2940 aaagtgctgg gattacaggt gtgagccact gcgcccggcc ctgggatcct g tgttttgaa    3000 tgaggctcct cagtactcgg ctctactggg gtcccagccc aaggaatagg a ctcagcctg    3060 cttctgtgcc acctgggct gcttgaactt tgcgacttgt ggcttgggag g agggaggtg    3120 gccgtgacct ttgggggttt ttgttctgcc tggctgtagc caccagcaga g ggggtgggg    3180 cacaggccag aaaaacccct tttgtggggt tgtgaggagt gacaattggc t gcttctcct   3240 ccccttccag gctcagagca gggctggggg gcagttgtgg gcagtgacca g ggtcagacc   3300 acctgggcgg aggttcagca tgaacttgca atgccctcca tctctccaaa a ctgggggac  3360 ccagcccagg gagggtgtgg gggttcctgg ggaagctggt ctaggcttct g ctcctgcca   3420 cggaccagct gtgtgatgct gggcacagga tgcactttct ctgggcctcc g tggcctctt  3480 ggggatggct tgcacgagat ccctccagtc ctgagtgaga ggctgtgcc t tgggaatt   3540 aagggtgcag gtggcgctca ggtgtccgag aagccatggg agccgggggc t gcagggatt  3600 ggacagagag gacctggta ctcgcatctg ttctcagacc acatctggaa t tgtagctcc    3660 ctctggaggg aggcaggagg tctcagcctt tcttgggggg cggtggcacc t gcgctgctc   3720 gctccacccc tgctctcacc tcccgctgca gtgctggcga gcccatcag c ccttcactc    3780 atctctaccc tccttctttc tgcctgggac acttgttttc atcctgggca g gccaggggc    3840 cagggcagct gttgggaatg tggcctgtgc catctccttt tttgctggga t cagaaaaca   3900
```

```
atcgcttaga attccaaggc aagggtgtga gcgcctggcc agccagtggg a acagacaac    3960
agcctgggag aggaatttcc agcctctctt cagtgtgcgt gtctggaaat g gggaccttg    4020
ccttgagcct ccagagttga acccagac acccaggaaa ggccctttgg g atttagccc    4080
agccacagta tgtcctaacc gtgaccttgg gcaagtaact caatctctcc g tgcctcagt    4140
ttccacaaag caaggataac actgggttgt tggaagaatc aatatagata t tgtctggag    4200
ggatgtaggt acagtgcatg gcattgggtg gcactcaaat gtcagctaat a atattatta    4260
ttattctacg ggaagaagac atcaggggaa gttgcagagc agcctgtggg c ggactctgg    4320
aacaagaggc tgaggcagtg cagcagaggg tctcagacgt gagcgctctc t gccccggaa    4380
tgattgactg agcgcaaagg tctgcacgct ttctctgtaa agggccagat g gtaggaatt    4440
tcaggctttg tggactgtat ggtctcagtg acagctactc aaacctgcct c tgtagcaag    4500
aaagcagcta catgcataga cagcacacac ccaactgaga gtggtgtgtt c ctatctaat    4560
tgtgctactg gacacccaaa cttgagcttc ccaccattcc atgtgccgca a attattctt    4620
tttttttgag atggagtttc actcttgttg cccagcctgg agtgcagtgg c tcgatctcg    4680
cctcaccaca acctctgcct cccaggttca agcgattctc ctgcctcagc c tcctgagta    4740
gctgggatta caggcatgag ccaccacgcc agctaatttt gtattttag t agagacggg    4800
gttttgccat gttggtcagg ctggtcccca actcccttcc tcaggtgatc c gcctgcctc    4860
agcctcccaa agtgttggga ttacaggcat gagccaccaa gcctggccac a aattattct    4920
taaacatttt tttttcaacc atttaaaaca tgaaaaccag tggggtgtgg t ggtgcacgc    4980
ctggtatccc agcactttgg gaggccaggg taggaggatg gcttgagccc a ggagtacaa    5040
gaccagcctg ggtaacatag cacaaccctg tctctacaaa caatcgacaa c aaaaaaatt    5100
agccaggagc agtgacacgt gcctgtggtc tcagctactc aggaggttga g gcaggagga    5160
tcacttgagc ctggaaaatc gagggctata gtcagctatg attgtgccac t ccactcctg    5220
cctgagcaac agggtgagac cctgtctcaa aaaaaaaaa aaaaaaaaaa a gtgaaaacc    5280
attcttagtg gcaggctgta ctgggcctct gggcaatcat ttgcctagtt c tgatttaac    5340
aaactcttgt atggagttta ctatgtaata ggcattgttt taagcacttt a caaatattc    5400
agccatctaa tcttcacaac aaccctatga ggtaggctat tattctccct t tatagagta    5460
aaaaaaaaaa aaaaggcaca gagaggttaa gtaacttgtc caaggtcaca c agcaagtga    5520
gtggtagagt catgatttgc acttgtgtgg cctgggttta gagtccacac t cttggttgc    5580
taggctgggc catgtctccc tgtgcagatg gggtgaagga agctgctttt c cttctactc    5640
ccttatgcaa aataaggatg aaaatcctgc cccacctcta agactatttg g tgaacaggg    5700
ccaggtattc tctgccctca taggacactc tagtagagca gctgggtgct a ataacagaa    5760
acacagaaac cacggagaat cacacctccc aaaaagtgcc gtgtgtggaa a gaacgtgca    5820
agggtgggca gaaacgtcac gtaaactgag aagtgctgat ggcaggaggt g tggatggca    5880
gtgggaagga agaggggaag aaagagctgg ctggtgggct gactgctctc c cctaccacc    5940
ccctgcccat ccagcctcac ttgcctgccg ataaggcccg gggtacacag g gccccgagc    6000
agcagcacct gctgatcaca gcgccgagct ccagcagcag ctccctggag a gctcggcca    6060
gtgcgttgga cagaagggcg cccactcgga accagccaca ggcaccaggc g tggaggcca    6120
gtggggccgg ggaggcccgg gccagcaccg ggagctcagg taagaggtgg g agcacacct    6180
ggcttcttcc caagcctcct tggtcttcct cacctggttt ctgtcttagc c atctcctcc    6240
```

-continued

```
tgagcctccc cgcagggtgg gacgaggcct gagccacagg gaacttcctt c ggttcgctg      6300 aacctaagtt ccctcccgcc tttgcccatg ctgggcctat cacctcaaaa t cctcccttc      6360 tgtgggacaa ccccagcttg tccaagtccc tggtatctgg gggaggagtt t tcctgaaac      6420 cttctccctg ctaccacccc cagctggcct ggctgctcct ccgggctcac c atgccctgg      6480 cctccctttc acaggactgt cagactgcat gtacagacat tgtcttctcc t gtctcccac      6540 gccaggctgt gggacacctg gtgagcctgg atcatctcat tcatccctgt a tctgcaggc      6600 ccaacacggc ccagctactg ataattaatc ataacaatcg cttctactta t ggaaggcta      6660 cggaacagca ggcactgtac tgggcacttt acatgcataa aactgacctg c atgtcaatg      6720 ctaagagata gttcctgttg ttatcccatt ttacagatga ggaaactgag c cccagagag      6780 gttaaacagc ttcttcaagg gcacatggct agtaaacaga agagccagac t caccccctag     6840 gctgtcgggc tccagagccc tgggattgga agatgaatga agaaatggtg g ctccagggc      6900 tccactcact gcagtttgtt gctgggtctc tttaggtctg aggcactggg a ctgtgggga      6960 ttgtgtccca tttatgcagg ctgcattgtg ccctggacct ggtctatgac a gatgtcact      7020 cctggttggc atctctaggg cccacactgg aggggcccct gtacagggtc t gctggcctg     7080 tgcctctctc cctcttacct ggcagtgcca gccagtgaga attcagggaa t gaccatgaa      7140 cttgggtcag tctgagatcc ttgcctggcc actctggtgc cataagaatt t gggtgggat      7200 gcttaaccct gccaagcctt ggttttttca cctagaggtg agctatagcg c ctccttgcc      7260 agggctggtg agagatgggt gacattgtgc ccagctgggc accagaccag g gccaggctc      7320 cctctgggcc gcctccaggt ggggactgat ggctgcagcc cccaccacgc a gccctcctc      7380 cagctcactc accccccagct gctccccagc tcactgcgcc cctgcctctt g cctgcactc      7440 atgccacccc tgcctgccac acctgttcct acctgccccc aactgcccac a ggagctgac      7500 gtggccattt ctgtctgccc catcatagcc cccagcctcc tcggtgggag g tctcatcag      7560 tgcccctcac tccatcctga gaactcccta tgggagggcc tgggccagtg c ctggaagag      7620 atcaggggcc ctacacactg ttgaatgaat gaatgaatga gtgcgctcca a ttataaact      7680 cttagtctttt gcccagttct tggattcgtc tgatttttttt tttttaaatg g ggtctcgct      7740 cgtcgcctag gctggagtgc agtggcgcag tcttggctga cttatctgct c accgcagcc      7800 tccgcctccc aggttcaagt gatcctccca cctcagcttc ccgagtaggc g ggattacag      7860 gcatgtgcca tcacgcctgg ctaacttttg tactttagt agagatggag t ttcaccatg      7920 ttggccagac tggtctcgaa atcctgacct caggtgatcc atctgcctcg g cctcccgaa      7980 gggctgggat tacaggcgtg agccaacatg cgcagcccat cttctgatt t cttagctac      8040 acctggtgtg gctccctcct tgggccaggg tggagccctg accatgtctg c cctcccctc      8100 tccctctgc cccttctgct ctgtgctcct tctcccgagt cccccagccc g tgtccctgg      8160 cctctgtctt ctcttctct ccctcccacc cctaacacct ccctccactg t gggaacctg      8220 taaaccccag ggttgtgccc cttcatggtc ccccatccac ccccgcaatg t ctcatgctc      8280 gatatacaaa ggccatggtg actttgggtg acatttgggt gctgtggagg c tcagggtgg     8340 aaatttcctt ccggccttgt gatttcaacc ctcctccccc accacatgct t gggctgtt      8400 ttgagcacag caggttgcca gctccatcca cctcccggct accctatccg a gtagttgga      8460 gttagggaga accaggctgg ggtgagggca ctcagcaggc cctgcagcga a cagcagcag     8520 caactctcat tttctgaggg ggctacttac tgtatgccag tcccttcata t tcatctcag      8580 caaacccacc gtccagtgcc tccccaacca gttagaaaac tcagttgccc a caggggctg      8640
```

```
ggcaggaagg tgaggcaaac cttgggctgt ccttggccgg atctcctgca t ctggctccc    8700
aagggaagcc ataaatccag attttaaat gtaaacgcct gaattttaaa t gttggtaat    8760
caattcactt aaaaacatca ccaccaccac caccaccacc aaacaaaaa a aacccgtag    8820
acttgtccct gttacaggca ctaggaacac agcagggaac aatcaaaaag t ccctggtct   8880
ggccaggcaa ggtggctcat gcctgtaatc tcagtacttc aggaggccaa g gcaggagga   8940
tcacttgagc ccaggagttc gagactagcc tgggcaacat agcaagaccc c cgtctctac   9000
taaaaaaata aaaaaaaag tccctaccct cctgggttca gagtctggtt g ggaccccca    9060
ggagctgggg gctctggaga tcaggagatc acagaaatgg ggagggaccc a gagagtggt   9120
ggataggatg gaagtaaat gtctctagag agggaggcca ggggtggag g gcgcttcgt    9180
ggaggaggtg gcctttgagc taaggcctga gcactagaga agagctctct a ggctgaggg   9240
agcggcctgt gcaaaggccc aggggacctg aagggctcaa ggggctgtag c aggggtgg    9300
ggaatgtggc tggaaggaac cccatcaagg tcttggagcg gcaggagagg g gtgggaga    9360
aggcaggctc cagatcagac agggcctggt aggctgtagc aaggactgtg g gttttgag    9420
cccccaagga agtgatctgc caggttcaag ggccagctct ggctgctgat g ggaaacaga   9480
tttcagaggg gtggggttga agccaggaca gatggaggct gttcacaccc a tccagatgg   9540
gagtgagggg aggcttccat agcccaccat gcagcagcag ggcagggtga c ccttgcaga   9600
agtcatcttt tgtttttgtt tgtttttgag atggagtttg gctctttcgc c caggctgga   9660
gtgaagtgac gtgatttcgg ctcactgcaa cctccgtagc ctgggttcaa g ctattctcc   9720
tgcctcagcc tcccgagtag ctgggattat aggcacctgc caccataccc g gctaatttt   9780
tttttttgta ttttgagtag agacagagtt tcaccatgtt ggccaggctg g tctcaaact   9840
cctgacctca gcgatccac ctgccttggc ctcccaaagt gctgggatta c aggcgtgag    9900
ccaccctgcc tggtccagaa gtcatctttt gaagggagac aaggcaggaa t gatggatgg   9960
gtgtgtgata tgagagaaag atgggtccga ggctctgggc ccaagcagct g ggtggatgg   10020
cagcaatggg aactgtgatg agcaggagag gttttggatg cgagatggga g tagaatcaa   10080
gagttaagtt ggaggctgag cacggtggct cacacctgta atctcagcgc t ttgcgaggc   10140
tgaggtaggc agattctttg aggtcaggtg ttcgagacca acccaggcaa c ctggcgaaa   10200
ccctgtctct acaaaaaatt agcagggtgc ggtggcctgt agtcccagct a ttcaggagg   10260
ctgatgtggg aggatcactt gaggccggga ggcagaggtc acagtgagtt g agggagtga   10320
cacagcactc ttttgagacc ctgtctcaaa aaaaaaaaaa aaaagacag a agagacagg   10380
gtctcactat gttgcccagt ctggtcttga actcctgggc tcaagcgatc c tacaaactt   10440
ggcctcccaa gtagacatct gttttatata attggctcct cccatctctg g ggtgattgg   10500
ggctgggtag gtagtgatgc tattcttatt cggcagaggg gaaatgagg c acatgcagg    10560
ttaagtgact tgctcaaggt cacacagcag agctgggcta gaatcttggt c tcggctcct   10620
ggcccagtgc tctttcccat gtgtctgaat ctgcatcttg gcagggtc c ctgggcccc    10680
actcctggac ccccggactg accccaccc catcttgtgc ttagcagatt c ttcccctgg   10740
tggccatggg acccaggtca atgtcacctg catcgtgaac gtctgtagca g ctctgacca   10800
cagctcacag tgctcctccc aagccagctc acaatgggga acacagatt c cagcccctc    10860
ggagtccccg aaggacgagc aggtcccctt ctccaaggag gaatgtgcct t tcggtcaca   10920
gctggagacg ccagagaccc tgctggggag caccgaagag aagcccctgc c ccttggagt   10980
```

```
gcctgatgct gggatgaagc ccagttaacc aggccggtgt gggctgtgtc g tagccaagg    11040
tgggctgagc cctggcagga tgaccctgcg aaggggccct ggtccttcca g gcccccacc    11100
actaggactc tgaggctctt tctgggccaa gttcctctag tgccctccac a gccgcagcc    11160
tccctctgac ctgcaggcca agagcagagg cagcgagttg tggaaagcct c tgctgccat    11220
ggcgtgtccc tctcggaagg ctggctgggc atggacgttc ggggcatgct g gggcaagtc    11280
cctgactctc tgtgacctgc cccgcccagc tgcacctgcc agcctggctt c tggagccct    11340
tgggtttttt gtttgtttgt ttgtttgttt gtttgtttct ccccctgggc t ctgccccag    11400
ctctggcttc cagaaaaccc cagcatcctt ttctgcagag gggctttctg g agaggaggg    11460
atgctgcctg agtcacccat gaagacagga cagtgcttca gcctgaggct g agactgcgg    11520
gatggtcctg gggctctgtg cagggaggag gtggcagccc tgtagggaac g gggtccttc    11580
aagttagctc aggaggcttg gaaagcatca cctcaggcca ggtgcagtgg c tcacgccta    11640
tgatcccagc actttgggag gctgaggcgg gtggatcacc tgaggttagg a gttcgagac    11700
cagcctggcc aacatggtaa aaccccatct ctactaaaaa tacagaaatt a gccgggcgt    11760
ggtggcgggc acctatagtc ccagctactc agaagcctga ggctgggaaa t cgtttgaac    11820
ccgggaagcg gaggttgcag ggagccgaga tcacgccact gcactccagc c tgggcgaca    11880
gagcgagagt ctgtctcaaa agaaaaaaaa aagcaccgcc tccaaatgcc a acttgtcct    11940
tttgtaccat ggtgtgaaag tcagatgccc agagggccca gcaggccac c atattcagt    12000
gctgtggcct gggcaagata acgcacttct aactagaaat ctgccaattt t ttaaaaaag    12060
taagtaccac tcaggccaac aagccaacga caaagccaaa ctctgccagc c acatccaac    12120
cccccacctg ccatttgcac cctccgcctt cactccggtg tgcctgcagc c ccgcgcctc    12180
cttccttgct gtcctaggcc acaccatctc cttttcaggga atttcaggaa c tagagatga    12240
ctgagtcctg gtagccatct ctctactcct acctcagcct agaccctcct c ctcccccag    12300
agggggtgggt tcctcttccc cactccccac cttcaattcc tgggccccaa a cgggctgcc    12360
ctgccacttt ggtacatggc cagtgtgatc ccaagtgcca gtcttgtgtc t gcgtctgtg    12420
ttgcgtgtcg tgggtgtgtg tagccaaggt cggtaagttg aatggcctgc c ttgaagcca    12480
ctgaagctgg gattcctccc cattagagtc agccttcccc ctcccagggc c agggccctg    12540
cagaggggaa accagtgtag ccttgcccgg attctgggag gaagcaggtt g aggggctcc    12600
tggaaaggct cagtctcagg agcatgggga taaaggagaa ggcatgaaat t gtctagcag    12660
agcaggggca gggtgataaa ttgttgataa attccactgg acttgagctt g gcagctgaa    12720
ctattggagg gtgggagagc ccagccatta ccatggagac aagaagggtt t ccaccctg    12780
gaatcaagat gtcagactgg ctggctgcag tgacgtgcac ctgtactcag g aggctgagg    12840
ggaggatcac tggagcccag gagtttgagg ctgcagcgag ctatgatcgc g ccactacac    12900
tccagcctga gcaacagagt gagaccctgt ctcttaaaga aaaaaaaagt c agactgctg    12960
ggactggcca ggtttctgcc cacattggac ccacatgagg acatgatgga g cgcacctgc    13020
cccctggtgg acagtcctgg gagaacctca ggcttccttg gcatcacagg g cagagccgg    13080
gaagcgatga atttggagac tctgtggggc cttggttccc ttgtgtgtgt g tgttgatcc    13140
caagacaatg aaagtttgca ctgtatgctg gacggcattc ctgcttatca a taaacctgt    13200
ttgttttaca cgtcgacccc tggctctgcc tggggtctgg gcttgggttt g tccatgctc    13260
ctacttgtct gccaccctg tgtaagggga gatgcgtca cggtccctgg a gtctggctg    13320
gccctgttg tgactggacc acagagggac ccctgttaca gccgcccct c aagcctgtg    13380
```

-continued

```
aaccataaga gaacttcctg ctcgggacca cacagctggc tgggttccaa g tgtgccctg   13440 gtctcatgcc ttcatcctcc aggtctcctg ggcctgctct caggaccggg a tggggtctc   13500 tgcagatccc tagcagccta ggcagccagg ctctgccctc ctggggaccc c actcgggga   13560 gagtggttgc ccctgggata ctcagaccag tacagggttt tggggcccca g aggacatcc   13620 ctgggcccag gtaggaggtt agaacagggt tctggagatg acctctgacc t cctcctgag   13680 ggatgagcag cagttttcca gaacaaagga ttgcagggaa ctgtcaggca a aaggagttc   13740 tgagtttaaa ggccttagcc tggccagcat ggtgaaaccc catctctacc a aaaatacaa   13800 aaaattagct gggcatgacg gtatgcacct ataatcccag ctagtcagga g gccgaggca   13860 cgagaattgc ttgaatcaag gcaacagagg ttgcagtgag ctgagatcgg g ccactgcac   13920 tccagcctgg gtgacagagt aagagtctgt ctccaaataa aataaataaa t aaaatcaat   13980 taattagaag aaagccttgg aggggagaga gaccttggcc tgtgtattgg t tccactgac   14040 cccctgggtc accatcgtca ctccagctcc tgtgactccc tcagtgggac c attttcatt   14100 cttggtgatt ataggatctg tgattgatgg aacgccccgc ctcctggctt c tcgccctcc   14160 tctcctccat ggtcctgtcc tccagcctgt ctcagtcact caacccttga c caaggctcc   14220 ccacacttat tccataaaga gccagggagc aaatttattt taattttttg a gacaaggtc   14280 tcactctgtt acccaagctg aaatgtgatc gtggctcact gcagccctga c ctccagtcg   14340 cagcctcttg agcagctagg actacaggca tggaccacta tgccgagcta a attttaaat   14400 ttttttattt ttattttttg ggtttccctg tgttgcccag gctggtctcg a actcctggg   14460 ctcaagtgat ccaccggcct gggcctcctg aactgctggg attacaggtg t gagccattg   14520 cgcctgacca gaatcaatat tttacacttg gcaggcctta cagtttctgc a acaaccact   14580 cacctgtgct gttgaagtgt gaaaacagct gtgcacagga catgaaagaa t gggcaggag   14640 gcggatgtgg ccttcggggt gtgcccatgc cagtgcctta gagcctggca t tactgataa   14700 ctgcacgcta atctcaattt caagcatccc acttcccccc accccctactt c ctcctgtct   14760 ttctccctca gtggcacctg cagctgttgg ttacgttttc tcccttgtac g cacccacgg   14820 cactttctcc tggtttgttg ttctctctct ggttgaaccc agctctctgc c tgtgccaca   14880 cctgcacgtc tgcacctggc tggggcagga tgatggcctt ccaccatgct g gctggtcgc   14940 gttttcattt catgatcatt agacttggct gggcacagtg gcttatgcct g taatcccag   15000 cactttggga ggctgaggtg ggcagactgc ttgagctcag gagttcaaga c cagcctggg   15060 gcaacatggt gaaaccctcat ctccacagaa aaatacagaa actagctggg t gcggtggca   15120 cgtacctgga atcccagcta cccatgaggt tgaagtggga ggattgcttg a gcccaggag   15180 gcggaggttg ttgtgagctg agatcttgcc actgcactcc agcctggggg a tggaaaaaa   15240 agaataaatt ctatggggggt ccttggtgct gcccagcagt gacaacaggt c ccctcccccg   15300 atatattagt tcctgttgtt gctataacaa accacacaaa ctcagtggct t aaaacaata   15360 caatttcatt ctcctacagc tctgggagcc agaagtataa aagcaaggtg t tgccaggcc   15420 tgctaggctc aaatggggaa tttgttcttg gaggctttag gggagaatct g attccttgc   15480 cttcagcttc cagcggtacc tgcattcctt gacttatggc cccttcgtcc a tcttcagag   15540 atagcaacgg aatctcttca gaagtcagat ctcccttttgc ctcccaagtg t agggacacc   15600 tg                                                                   15602
```

<210> SEQ ID NO 18

```
<211> LENGTH: 248
<212> TYPE: DNA
<213> ORGANISM: Homo sapiens
<220> FEATURE:

<400> SEQUENCE: 18
aatagccttc ccagctgggc tttagaactc tggactttgt ggggacagtg g atgagccca    60 gggtcctggc agaaggctcg cccagctgag acctctggcc cttgtttcct c aggccaaca   120 tgcaaaagtc ttctgtacca agacctcgga caccgtgtgt gactcctgtg a ggacagcac   180 atacacccag ctctggaact gggttcccga gtgcttgagc tgtggctccc g ctgtagctc   240 tggtgagg                                                             248

<210> SEQ ID NO 19
<211> LENGTH: 519
<212> TYPE: DNA
<213> ORGANISM: Homo sapiens
<220> FEATURE:

<400> SEQUENCE: 19
ctgtgttgcg tgtcatgggt gtgtgtagcc aaggtcggta agttgaatgg c ctgccttga    60 agccactgaa gctgggattc ctccccatta gagtcagcct tccccctccc a gggccaggg   120 ccctgcagag gggaaaccag tgtagacttg cccggattct gggaggaagc a ggttgaggg   180 gctcctggaa aggctcagtc tcaggagcat ggggataaag gagaaggcat g aaattgtct   240 cttaaagaaa aaaaaagtca gactgctggg actggccagg tttctgccca c attggaccc   300 acatgaggac atgatggagc gcacctgccc cctggtggac agtcctggga g aacctcagg   360 cttccttggc atcacagggc agagccggga agcgatgaat ttggagactc t gtgggcct   420 tggttccctt gtgtgtgtgt gttgatccca agacaatgaa agtttgcact g tatgctgga   480 cggcattcct gcttatcaat aaacctgttt gttttaaaa                           519

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
tctccaggct ccgctgcgct                                                 20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
ttgcatgttg gcctgaggaa                                                 20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
ctgagccggc atgtgctccc                                                 20
```

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ttctctgagc cggcatgtgc						20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ctgtctggtc atagtattct						20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
tttaagagac aatttcatgc						20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
cacatctgag ctgtctggtc						20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
gcagcacatc tgagctgtct						20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
gcatgttggc ccggcgagca						20

<210> SEQ ID NO 29
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 29
gaagactttt gcatgttggc                                           20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
cagctcaagc actcgggaac                                           20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
tccacctggt cagagctaca                                           20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
ggtgcagatg cggttctgtt                                           20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
gtttcagttc ctggtctggc                                           20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
gatgtttcag ttcctggtct                                           20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
tgcacaccac gtctgatgtt                                           20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
cacgttacag atctggtggg                                          20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
gggtaagtgt actgcccctg                                          20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tgttgggatc gtgtggacac                                          20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
gctgcgtgtg ttgggatcgt                                          20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
cacaatcagt ccaactggaa                                          20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
caagggcttc tttttcacct                                          20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gcaagtgagg caccttggct                                                                                  20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
cccgggcctt atcggcaggc                                                                                  20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
gtcccatcta cttgggaggc                                                                                  20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
ctccagggag ctgctgctgg                                                                                  20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
gagctctcca gggagctgct                                                                                  20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
tggccgagct ctccagggag                                                                                  20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
acgttcacga tgcaggtgac                                                                                  20

<210> SEQ ID NO 49
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 49
gtcagagctg ctacagacgt                                                    20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
tgtggtcaga gctgctacag                                                    20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gtgtctccca ttgtggagct                                                    20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
ctggaatctg tgtctcccat                                                    20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
tgtgaccgaa aggcacattc                                                    20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
ggcttcatcc cagcatcagg                                                    20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
```
actgggcttc atcccagcat                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
ccggcctggt taactgggct                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gtcatcctgc cagggctcag                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
agaggaactt ggcccagaaa                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ctaagcccag cagcccagct                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
tgggtgactc aggcagcatc                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
agtctcagcc tcaggctgaa                                              20

<210> SEQ ID NO 62
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 62
accccgttcc ctacagggct                                                  20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
gagctaactt gaaggacccc                                                  20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
ttagctgtgc cacactggga                                                  20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
cagcactgaa tatggtggcc                                                  20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
gttatcttgc ccaggccaca                                                  20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
cgttatcttg cccaggccac                                                  20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
agatttctag ttagaagtgc                                                  20
```

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
gcttgttggc ctgagtggta                           20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
tgtggctggc agagtttggc                           20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gcaggcacac cggagtgaag                           20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
tggtgtggcc taggacagca                           20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
attccctgaa aggagatggt                           20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tctaggctga ggtaggagta                           20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 75
ggccatgtac caaagtggca                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
gactggcact tgggatcaca                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
ctacactggt ttcccctctg                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
gacaatttca tgccttctcc                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
tggtaatggc tgggctctcc                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
tctgacatct tgattccagg                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
gcagaaacct ggccagtccc                                              20

<210> SEQ ID NO 82
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
gtccaatgtg ggcagaaacc                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
tctcccagga ctgtccacca                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
ggctctgccc tgtgatgcca                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
caaattcatc gcttcccggc                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
aaacaggttt attgataagc                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
ctacagaggc aggtttgagt                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
```
agacagggtt gtgctatgtt                                           20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
tggcacaatc atagctgact                                           20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
gatggctgaa tatttgtaaa                                           20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
agggagaata atagcctacc                                           20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
agccttccat aagtagaagc                                           20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
ccaagttcat ggtcattccc                                           20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
tgaattgatt accaacattt                                           20

<210> SEQ ID NO 95
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 95
caccttgcct ggccagacca                                              20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
gaagtactga gattacaggc                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
gtccccagga gggcagagcc                                              20

<210> SEQ ID NO 98
<211> LENGTH: 5874
<212> TYPE: DNA
<213> ORGANISM: Mus musculus
<220> FEATURE:
<221> NAME/KEY: unsure
<222> LOCATION: 1188
<223> OTHER INFORMATION: unknown
<221> NAME/KEY: unsure
<222> LOCATION: 5837
<223> OTHER INFORMATION: unknown
<223> OTHER INFORMATION:

<400> SEQUENCE: 98
tggatccctg cttttcagta ttacctaaac catacatgct ctagttacct t aatgtgaaa    60 aagtgtaaag cttttggggt aacacacact tttgcttgta gactttgagc c atctttata   120 tggtacttct aataccttta tgagtttaga gaataaacaa taatgtcgag a aaaaaagtc   180 tgtatatgtt caatacgcac actcaatgta tttttcttgt ttgcttccta g aacatgtct   240 gatcccttttt actgttgagt aaaccgtaga tatggagccc acagatctga g gcctccctg   300 aaatcctctg tgttattttt cactactaagg cagaaaatag tctagagaaa c gttaaactc   360 aaagcagttg tccttgggaa gaaattgcat gagtgagaac tgtagcttag a ggcaaagac   420 atctagttta atgataaagt gaagagtgt ggaataaggg gctggagaga t gtcttggcg    480 tttgttaaga gtgtttgcca ctcattcaat tcaaaggact cgagttcagt t cctagcacc   540 tataacatta gccttagagg gatgtgtggg ccactcgtgc acatgcgcat g tatatgtat   600 atgtgtctat gtatgtgtat gtctgtgtga atgtgtattt gaatgtgtgt c ggggatgta   660 gaggtccaag gtggtaatag gatgagtttt ctgcagccat tcttcactgg a ttggactat   720 ctggctagct agcttgccct caggctctgt tgtttccacc tctcacatgc t gggagaaca   780 aattggctac cacacccaca cagcatctgg tgagtgctgg ggatcagggt t ctagtgttc   840 aagctcttgg ggaaaacact ttacccattg aactctgtct atctatttat t tatttctct   900 ttaaaaggca tgtactgatc atacatttaa aagcctataa cacagctata c acaatgtac   960
```

-continued

```
agtaatctgt tccttagatg ccagtccagc aaaggctctt agataatgat t tagcaataa      1020 atactggcca aacagctgtt tttttttttt tttttttttt agagaccggg a aaagacaac      1080 tcagaataga aattttgaat gtctcctaac aaccttctcc caaatgactg g gtcctcttt      1140 gaggcccaga ggtgggaaga tttgtgcccc taagcagggg tgaccctntt c ataaggaga      1200 tgaggatgga gacactgttt tggggggtca acactccacc tcccagcatg a atgctcagc      1260 gtacgccaag agatgcatgt tgtgtgtgtg tggtgtgcat gtgcacctca g aggcataca      1320 tgttcatcga gacaagaaga gatgcatgtt gtgtgtgtgt ggtgtgcatg t gcacctgag      1380 aagcacacac atgttcatca agaccagaag ttaatgtcaa gtgtcttcct c aattctcaa      1440 tattttgagg tacagtctct cacttgagcc cagagctcac ccatttgact g gttctaact      1500 agcacacttc acagattctg tctctacctc ccgagtctaa gatacaggag g accacaata      1560 tccactatgg ttttttagcc ctccccgatg ggtgctgggg atgcagacat g ggtctcatg      1620 cttgcatact tgcatgcttg catggcaagt attcactgta ccatcttacc a gaccctaga      1680 tgacctgaca ttttcttttt tctctctctc tttttttaa gatttactta t ttatcttta      1740 tatatgagta cactgtagct gtcttcacac acaccagaag agggcatcag a acccatccc      1800 attagagatg gttgagagcc accatgtggt tttggggaat tgaactcagg a cctctggaa      1860 gaacaatcag tgctcttaac cgctgagcca actctccagc ccctgactgt t attttgttt      1920 gtttgtttgt ttgtttgttt tgttttgttt tgttttttt atgataccaa a tacgcacgc      1980 acaccttgac tgaagaaacc atcagagggt tgaggtgcag cagagagtgg c ttgtgtgct      2040 gggggaggca gcttctacta agagagagaa tctctgatgt tcttttctga a tgaactcct      2100 aggaacagcc acaaagcaag ctctttccaa catggcctct agaggcccaa g atattataa      2160 ctgcttctag gcaatgagat tcccttgttc tccttctcc agtggtccca g ccagacctt      2220 tattgcctga ctctttgcct gtgcttatct ctacaccttg tgctgggcca g ccccttggt      2280 gagtcacaga ctaaaatcac gagcaggaag ctgtgttagc cacagactca c aactgtctc      2340 ccctggttgt cctcccacct gtatccccag acacatacac gcacatgcac a cacaccaca      2400 ccacacggta gtagaaggct ttcttttctag aaaacaacgc agctgagaca a aaagagtcc      2460 accacagcaa ggtcaatgga cagttacatt tccattaatg gaaatggggt g gggaaggct      2520 cacctgactc tccagccact cctccaagag ctctatccaa attgctcctg g gggactcgc      2580 tgtgtccctg gaagaactag tgtacttgac tgtggacgac tataagagga a ctctgtgca      2640 attgcatgga agccactaac cttgctgcgt gaagactttc cggtgcagct g ccttgggt      2700 caccatgctc tctgtaggaa agtccaacaa acttgttggt tccccagggt a aacttggtt      2760 agaatcatgc tttggtttgt cattagaacc ttatgaggag tgggataggc c aacacaggc      2820 acatcacatg aacaagccca ataaaataaa ataaagtca taggatgctg g cactgggt      2880 tttgtaaata gagtttctgg cacattctct ctggttgtat acaggtggcc a tgtcagaag      2940 tgaagcctgt gttggtgaag ctggagtctt cctccagagg cttgccaggc c aactgcata      3000 cagtaagtgc tcagttagca gcctgagcac ccctgcttgc tttgcctttc a aaggtgagt      3060 cttctgtttg cagaagcaga gatgtcagct tgttggagtg tgagatgata g ggttgggac      3120 tgtcctggga agtggggagg taccagatta agatgatccg tctgcgaccc t tatgaaatc      3180 caccatccta tctctgctga ctgatataag aacaatggga ccttttctgt a ctgtgggc      3240 ttatggacta aaaggtgaat ggtggggttg atagagccaa gcactgactg g attagactg      3300
```

-continued

```
gattccaacc ctgatatata cctagccatt cgttaatgtt ccccacttgg t gttttgaga    3360 caaggtttct ctatatagcc ctggctgtcc tgatattcgc tatatatatt c actatatac    3420 atcaagctgg ccttgaactc tctgagatct tcctccctag ggctggaatt a aaggcatgc    3480 accaccacgt ctggttaaca ttcatctctt tattgtctct tgtgtatact t agcagaagt    3540 cctcacttac ttccatttta ttgagctgtc cttattgtgt gttccctagg c accaaggga    3600 atagccagaa caggatggtg tacctgtgtc ctagaggagt atataatgtg a cagagtgaa    3660 cagtgactgg gctgtgtagg agctccttga cttttgaaggt aactaaactg g gtttgaatc    3720 aacatactcc ctcctagctg tgaaaggtcc tataaaactt catctccccc c acccctgct    3780 cctgcaagac cacatgtacc agcagacata tgttgctgac cctaagtagt a gtcttccag    3840 taactgctgg tttcacaact actaagtgtt atcagtgtga atagcaagtg a tccctggtg    3900 aagatttgca aggcacctgc acaggtgcta agttagctgt cagggattgg g ggggggggg    3960 gggttggggg gtggcaggtg ggctgtcagg ctgtactatt ttcacagaat a acagctgat    4020 gctatatcgt aagtagcatt ttaaaaaaat catcagggta gagctgctgt g attgctatt    4080 ggcggcttta taagaagaaa aagagaaaca caaacacaca cacacacaca c acacacacc    4140 atccttatct cttactatgt agtttttgcc accaaggcta tcgtcagcta t gttccatta    4200 acgttggatg agaaccatga aactaagtca cccccttctc ttcaaagtgt a tgaggtgtg    4260 tgatgctgaa ccacagaata cagactaagt taggaaccag cctttcgtct c ccacatgtg    4320 attcttggtg gcattgttac ctggctggag agaatgagta aattggaccc a ctgggcaga    4380 atccagggca gaccactgaa tcttgcttct gacagatgac actggctttc a gctttctca    4440 gatagaccag ggcacctcct ccacatgtct tccacaggag gcttaaagac c agaaccctc    4500 cctgcctgct cagtggctac ccctcttcag ggttgaggtt ttggagctga g acctatgtc    4560 tcagaaacat gtgagaacca ggtgatttcc caggctcctg accagcaggt g ggattttcc    4620 atcctcccaa gggtcacttc ccagtttctc ccccagcacc taaaagtacc g tccttgagg    4680 tggccctaca aggaccagtg gctgcagggt ctctcagtat ctctatcagc c tacagtgag    4740 agtgtgtgtg tccatgaagg agggacagaa tagttgcctg cctccctacc c accctacct    4800 ctccaaatac tccatattca gggttgtagg gatatcgact gtccttggga g cttgctgat    4860 gaggtcagtt ctaggaagca agactttctg gatggtttc ttcctcgatt t ctgtttacc    4920 tatcagccaa gagaactcag aaaaagagga ctgctcttac ttagggttcc a agtatgttt    4980 aaggaaaaaa tgaaacatat taaaagagc tatacctatg caatgctgct t atactatgc    5040 ctgtacactc cgagtaagca gacatatgct gcacgttata ggagccatat t atatagctc    5100 atattaataa gctccatgag aagatgcaaa cattcatgtg gagttagcct g gctctagaa    5160 ggctttggtt ctcctgagcg gtgccaactt tgggactgct tccccccat g tcctaccac    5220 gaagagtagg aagtccatga gatctgggac gggctgatgg tgacaaatta g ctggggag    5280 gcccaatcag ggcacccagt cacgaatata gtggacacct cgccagtctc ttcccccacc    5340
actggaaggg tgtctcgaag aggaaggagt gatagaagct cattcattcc c ggaagagat    5400 gctggagaaa gaggcccaga gatgccagg aatcacaggt ggaggtgtcc t gcgagggc    5460 gaggactctg tgtaaagagg cgtgtcctca gggcgcggcc ccgcccattc c cgccctccc    5520 cccaccccct ggtctgccct agctcctggc ctgagggttt cgctttcagt c accagctag    5580 agcgcagctg aggcactaga gctccaggca caagggcggg agccaccgct g cccctatgg    5640 cgcccgccgc cctctgggtc gcgctggtct tcgaactgca gctgtgggcc a ccgggcaca    5700
```

-continued

```
cagtgcccgc ccaggtgggt gactcttggg gtcacggggg acagctgcgc a tcacaaagt     5760 gcccattcca gctactgcta ctgcacaatt ccgggacagc atgagaggcc a tcacgtccc     5820 cagcaaacac gccacgngcc tttggggacc actggggacc cgaggtctgg c cgt          5874
```

<210> SEQ ID NO 99
<211> LENGTH: 1003
<212> TYPE: DNA
<213> ORGANISM: Mus musculus
<220> FEATURE:

<400> SEQUENCE: 99

```
tttgtgtgga ggtctttgtc acagtgagtc aagccactgt cttaaaaaaa c tacatcttc      60 tcagagcctt gctgggtctc acccagcagg caggagggaa gccctaaagt a acccacttc     120 ctggcccagc aaactgcaga cacagcgtgc acctgaagag gagcagagga a agctgctct     180 actctctcag ctctcgtctc cacgaaacca tcatgagctg gtgacagtat g ctggagccc     240 aagagtcata ctgatggctg cctcccttgt tccttccagg ttgtcttgac a ccctacaaa     300 ccggaacctg ggtacgagtg ccagatctca caggaatact atgacaggaa g gctcagatg     360 tgctgtgcta agtgtcctcc tggtgagagg cagctgctgg ggctttggaa g ctggtgcat     420 ggagggcatg cttgtctggg aatgagggcc ttcagctctc acttggctgc t ttatacatg     480 ctagggttca tgattcatct tgccctgggc cctgggtctc gcaagtgctt g tccctccac     540 tgagcacact tctcagtgtc ttctcctggt tactgcctac ctacattttg a ccctatcct     600 ctgccaggaa gcctcctcaa tactgcaatg atgtccctag cactttcata g cccactatg     660 tgcctatgtc ctcaccctat tgagtagtga gtgtagcttg gtccctgtga g ttccaagca     720 cacggctggc ctatattgat gtcctgtact taattgtcaa gtaaaatgaa t ggatagcca     780 tatcatagat ggcggatctg agccctggcc tcattggcga ggactgagta g ctgccccag     840 tgccgagtag cacaatcaag tgtagcattc aattaagtcg tatttataat g catctactc     900 tgtgctcaac ctgctgagag gaaagccaca caaacacggg atacagcagg c tgggaagta     960 agtgcaaagc cctaaagcag gggcctgttt taatgggtcc aaa                      1003
```

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100

```
cttgtgcctg gagctctagt                                                   20
```

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101

```
agctgcagtt cgaagaccag                                                   20
```

<210> SEQ ID NO 102
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 102
cagctgcagt tcgaagacca                                              20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
tagggtgtca agacaacctg                                              20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
gtttgtaggg tgtcaagaca                                              20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
tacccaggtt ccggtttgta                                              20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
gaggacactt agcacagcac                                              20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
acatattggc caggaggaca                                              20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
ctgcagctca aacatgtacg                                              20
```

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
tccacctggt cagtggtaca                   20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
ccagaatggg ttttcaaggc                   20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
gccagggccg cacttgctca                   20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
cttgaactgg ccactccgaa                   20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
gatgtggtgt cagagaacgt                   20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
gtggatgatg tggtgtcaga                   20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 115
gatgctacag atgcggtggg                                              20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
ggaatagcca ggatgctaca                                              20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
gcatctgtgc ttgcatttcc                                              20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
ctctggctga gatacgtaga                                              20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
tgtgggctct ggctgagata                                              20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
ggatcttgtg ggctctggct                                              20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
ttggaagaga gatgccaccc                                              20

<210> SEQ ID NO 122
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
gaccaattgg aagagagatg                                          20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
caatcagacc aattggaaga                                          20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
acaatcagac caattggaag                                          20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
cctaacatca gcagacccag                                          20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
tttcctctgc accaggatga                                          20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127 cttcttttc ctctgcacca                                           20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
```

```
gagggcttct ttttcctctg                                              20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
ggagggcttc tttttcctct                                              20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
gtaggcagga gggcttcttt                                              20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
cacatgaggc accttggcat                                              20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
ggcacatgag gcaccttggc                                              20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
ggagctgctg ctggaactgg                                              20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
tgggaagaat ctgaaatcct                                              20

<210> SEQ ID NO 135
<211> LENGTH: 20
<212> TYPE: DNA
```

<213> ORGANISM: Artificial Sequence
<220> FEATURE:
<223> OTHER INFORMATION: Antisense Oligonucleotide

<400> SEQUENCE: 135
gggtcaggcc actttgactg     20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
tagctcctta gaaggaaaaa     20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
tgcagtgtca gcattcaggc     20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
ccacttgctc ctacttgctg     20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
agagggtact tcctaagagt     20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
gattcttgca tcaaaagaat     20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
cctataacag agcaactctg     20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
gtgttgctga ggatcaaacc                                              20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
tcattagaag gtcaggagga                                              20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
aaggaaggcg tggccttgga                                              20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
actcacagtg cctaacccgg                                              20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
ctgttccaac tcacagtgcc                                              20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
agagctggct tcagctgttt                                              20

<210> SEQ ID NO 148
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 148
catgaatcct ttggcaaaag                                               20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
ctgccaagtt catatccagt                                               20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
tatcttgatt ccagagtgct                                               20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
gagccttaac aagtcggccc                                               20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
ctgatgctgc agagccttaa                                               20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
tccttagcac accctttagg                                               20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
atttataagc aggaattctg                                               20

```
<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
cacatacatg caaacatgga                                               20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
agtaactgga gagtgatcaa                                               20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
gcccgcctca gtaactggag                                               20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
gcaagctctg ggtacagatg                                               20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
agcactccat aggcagacag                                               20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
gcagcctgcc tgtaacctga                                               20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 161
taaatgtcgg gcaggtatgg                                               20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
aaaatgcagg tatacaagtg                                               20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
gccatcttgc cagttcaaaa                                               20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
tgatgtgtgc acatatgcag                                               20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
acatttatgg tatgtgagtg                                               20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
gtccaatcca gtgaagaatg                                               20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
tgatcagtac atgcctttta                                               20

<210> SEQ ID NO 168
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 168
agtcaagtac actagttctt                                              20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
agtccataag ccccacagta                                              20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
agtttagtta ccttcaaagt                                              20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
tggattctgc ccagtgggtc                                              20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
caaaacctca accctgaaga                                              20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
gaggaggctt cctggcagag                                              20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide
```

-continued

<400> SEQUENCE: 174
acatcaatat aggccagccg                                                     20